(12) United States Patent
Vigh

(10) Patent No.: US 6,391,862 B1
(45) Date of Patent: May 21, 2002

(54) CHIRAL RESOLVING AGENTS FOR ENANTIOSEPARATIONS

(75) Inventor: Gyula Vigh, Magnolia, TX (US)

(73) Assignee: The Texas A&M University System, College Station, TX (US)

(*) Notice: Subject to any disclaimer, the term of this patent is extended or adjusted under 35 U.S.C. 154(b) by 0 days.

(21) Appl. No.: 09/172,575

(22) Filed: Oct. 14, 1998

Related U.S. Application Data

(60) Provisional application No. 60/063,998, filed on Oct. 14, 1997.

(51) Int. Cl.[7] .................. A61K 31/715; C08B 37/16; C07H 15/04
(52) U.S. Cl. .................. 514/58; 536/103; 536/120; 536/122
(58) Field of Search .................. 514/58; 536/103, 536/120, 122

(56) References Cited

U.S. PATENT DOCUMENTS

| | | | |
|---|---|---|---|
| 4,020,160 A | | 4/1977 | Bernstein et al. ........... 424/180 |
| 5,134,127 A | * | 7/1992 | Stella et al. .................. 514/58 |
| 5,154,738 A | * | 10/1992 | Armstrong et al. ............ 55/67 |

(List continued on next page.)

FOREIGN PATENT DOCUMENTS

| EP | 893453 | * | 1/1999 |

OTHER PUBLICATIONS

Cavitron® product literature, published by Cerestar USA, Inc., Aug. 1996.*
Wenz, Gerhard. "Cyclodextrins as Building Blocks for Supramolecular Structures and Functional Units", Angew. Chem. Int. Ed. Engl., vol. 33: 802–822, 1994.*
Duchene et al. "Pharmaceutical and Medical Applications of Cyclodextrins", Chapter 19 of Polysaccharides in Medicinal Applications, publ. by Marcel Dekker, Inc., pp. 575–602, 1996.*
T. Christians et al., "New single–isomer chiral selector for capillary electrophoresis: the highly water–soluble *heptakis* (2–N,N–dimethylcarbamoyl)–β——cyclodextrin", J. Chromatogr. A, 911 pp.249–257, (2001).
W. Zhu et al., "A Family of Single–Isomer, Sulfated γ–Cyclodextrin Chiral Resolving Agents for Capillary Electrophoresis. 1. Octakis(2,3–diacetyl–6–sulfato)–γ–cyclodextrin", Anal. Chem., 72, pp.310–317, (2000).
H. Cai et al., "A Family of Single–Isomer Chiral Resolving Agents for Capillary Electrophoresis. 3. Heptakis (2,3–dimethyl–6–sulfato)–β–cyclodextrin", Anal. Chem., 70, pp.580–589, (1998).
P.V. Bondarenko et al., "Characterization of Single–Isomer, Heptasulfated β–Cyclodextrins by Electrospray Ionization Mass Spectrophoresis and Indirect UV Detection Capillary Electrophoresis", Anal. Chem., 70, pp.3042–3045, (1998).
S.R. Branch et al., "Effect of β–cyclodextrin acetylation on the resolution of phenethylamines with capillary electrophoresis and nuclear magnetic resonance spectroscopy", I J. Chromatogr. A., 758, pp.277–292, (1997).

(List continued on next page.)

*Primary Examiner*—James O. Wilson
*Assistant Examiner*—Leigh C. Maier
(74) *Attorney, Agent, or Firm*—Baker Botts L.L.P.

(57) ABSTRACT

A cyclodextrin composition of substantially pure, sulfated-cyclodextrin derivatives particularly suitable as chiral resolving agents for enantioseparation by electrophoresis. The cyclodextrin composition preferably have an isomeric purity of at least 80 mole %. Non-sulfato substituents for the substantially pure cyclodextrin derivatives are hydrogen, $C_1$–$C_{12}$ alkyl groups, $C_2$–$C_8$ hydroxyalkyl groups, $C_1$–$C_{12}$ alkylnitryl groups, $C_2$–$C_{12}$ acyl groups, aryl groups, carbamate groups, thiocarbamate groups or combinations thereof.

17 Claims, 28 Drawing Sheets

U.S. PATENT DOCUMENTS

| | | | | |
|---|---|---|---|---|
| 5,180,716 A | * | 1/1993 | Yaksh et al. | 514/58 |
| 5,183,809 A | * | 2/1993 | Weisz et al. | 514/58 |
| 5,198,429 A | * | 3/1993 | Konig et al. | 514/58 |
| 5,288,916 A | * | 2/1994 | Lorenz et al. | 568/324 |
| 5,385,891 A | * | 1/1995 | Moriya et al. | 514/58 |
| 5,658,894 A | * | 8/1997 | Weisz | 514/58 |
| 5,760,015 A | * | 6/1998 | Joullie et al. | 514/58 |

OTHER PUBLICATIONS

J.B. Vincent et al., "A Family of Single–Isomer Chiral Resolving Agents for Capillary Electrophoresis. 1. Heptakis (2,3–di–6–sulfato)–β–cyclodextrin", Anal. Chem., 69, pp.4226–4233, (1997).

J.B. Vincent et al., "A Family of Single–Isomer Chiral Resolving Agents for Capillary Electrophoresis. 2, Hepta–6–sulfato–β–cyclodextrin", Anal. Chem., 69, pp.4219–4228, (1997).

S.R. Branch et al., "Chiral discrimination of phenethylamines with βcyclodextrin and *heptakis* (2,3–di–O–acetyl)β–cyclodextrin by capillary electrophoresis and NMR spectroscopy", Journal of Pharmaceutical & Biomedical Analysis, vol. 12, No. 12, pp. 1507–1517, (1994).

Lipkowitz, et al., *J. Am. Chem. Soc.*, 114, 15540 (1997).

Vigh, G. and Sokolowski, A. D., *Electrophoresis*, 18, 2305 (1997).

Williams, B. A. and Vigh, G., *J. Chromatogr., A.*, 777, 295 (1997).

Endresz, et al., *J. Chromatogr. A.*, 732, 132 (1996).

Fanali, *S.J. Chromatogr. A.*, 723 (1996).

St. Claire. R. L., *Anal. Chem.*, 68, 569R (1996).

Stalcup, A. M. and Grahm, K. H., *Anal. Chem.*, 68, 1369 (1996).

Szeman, et al., *J. Chromatogr., A.*, 728, 423 (1996).

Wang, F. and Khaledi, M. G., *Anal. Chem.*, 68, 3460 (1996).

Gahm, K. H. and Stalcup, A. M., *Anal. chem.*, 67, 19 (1995).

Weseloh, et al., *J. Microcolumn* Sep., 7, 355 (1995).

Camilleri, P. et al., *Chromatographia 38*, 771 (1994).

Sahota, R. S. and Khaledi, M. G., *Anal. Chem.*, 66, 1141 (1994).

Harata, et al., *Carbohyrd. Research*, 222, 37 (1991).

Stalcup, A. M., et al., *J. Chromatogr.*, 540, 113 (1991).

Stalcup, A. M., et al., *Biomed. Chromatogr.*, 5, 3 (1991).

Armstrong, D. W., et al., *Anal. Chem.*, 62, 1610 (1990).

Nardi et al., *Electrophoresis*, 11, 774 (1990).

Stalcup, A. M., et al., *J. Chromatogr.*, 513, 181 (1990).

Takeo et al., *Carbohyrd Res.*, 187, 203 (1989).

Terabe, S., *Trends Anal. Chem.*, 8, 129 (1989).

Vigh et al., *J. Chromatogr.*, 484, 237 (1989).

Chankvetadze et al., Analysis of Charged Cyclomalto–oligosaccharides (cyclodextrin) Derivatives by Ion–Spray, Matrix–Assisted Laser–Desorption/Ionization Time–of–Flight and Fast–Atom Bombardment Mass Spectrometry, and by Capillary Electrophoresis, Carbohydrate Research, 287:139–155 (1996).

Luna et al., Fractionation and Characterization of 4–Sulfobutyl Ether Derivatives of Cyclomaltoheptaose (β–Cyclodextrin), Carbohydrate Research, 299:103–110 (1997).

* cited by examiner

CHIRAL RESOLVING AGENTS FOR ENANTIOSEPARATIONS

This application claims priority under 35 U.S.C. §119(e) from U.S. Provisional Application No. 60/063,998, filed Oct. 14, 1997.

FIELD OF THE INVENTION

The present invention relates to single-isomer chiral resolving agents for separation stereoisomers and, more particularly, to functionalized single-isomer charged cyclodextrins for separations of stereoisomers.

BACKGROUND OF THE INVENTION

The separation of stereoisomers (e.g., enantiomers) is generally considered to be one of the more difficult tasks in analytical chemistry since chiral compounds exhibit identical physical properties in non-chiral environments. As a result, conventional separation techniques such as gas chromatography (GC), high pressure liquid chromatography (HPLC) and capillary electrophoresis (CE) have been modified to provide a chiral environment to facilitate enantiomer separation.

One such approach in providing a chiral environment has been through the use of chiral resolving agents, such as cyclodextrins. In fact, electrophoresis has become established as a powerful method for the separation of enantiomers (St. Claire, R. L., *Anal. Chem.* 1996, 68, 569R) due in part to the versatility of various cyclodextrins as resolving agents in both acidic and alkaline background electrolytes (BE). Although significant improvements in enantiomeric separations have been achieved with native as well as derivatized neutral cyclodextrins, as recently reviewed in Fanali, S., *J. Chromatogr. A*, 1996, 735, 77, the analysis of noncharged enantiomers only became possible when charged cyclodextrins entered the stage (Terabe, S., *Trends Anal. Chem.* 1989, 8, 129).

However, charged cyclodextrins used so far are complex mixtures that contain a large number of isomers differing both in their degree of substitution (the number of charges per cyclodextrin molecule) and the loci of substitution. As a result, the use of these resolving agent mixtures is fraught with at least four distinct problems in any given separation. First, the number and loci of substituents on the cyclodextrin greatly effect the chiral selectivity of the system, in which the direction and magnitude of these changes cannot be predicted a priori (Weseloh, et al., *J. Microcolumn Sep.* 1995, 7, 355). As a result, when mixtures of different isomers of substituted cyclodextrins are used, the overall separation selectivity of the system can be reduced or eliminated (Weseloch, et al., *J. Microcolumn Sep.* 1995, 7, 355; Szeman, et al., *J. Chromatogr. A* 1996, 728, 423; Stalcup, et al., *Anal. Chem.* 1995, 67, 19). Mixtures of charged cyclodextrins also present the problem of kinetic band broadening when the finite complexation rates of the different cyclodextrin isomers are slightly different, which unavoidably decreases separation efficiency. Likewise, fundamental molecular level studies through nuclear magnetic resonance (NMR) spectroscopy (Endresz, et al., *J. Chromatogr., A*, 1996, 732, 132) or crystallographic analysis (Harata, et al., *Carbohydr. Research* 1991, 222, 37) or molecular modeling (Lipkowitz, et al., *J. Am. Chem. Soc.*, 1997,114, 15540), which are aimed at improving the level of understanding of the chiral recognition process, are rendered impossible with mixtures of resolving agent. Finally, resolving agent mixtures (commercial or otherwise) often differ between batches and thus compromise the reproducibility of difficult separations.

Accordingly, there is a need in the art for resolving agents that do not exhibit the deficiencies associated with charged cyclodextrin mixtures.

It is, therefore, an object of the present invention to provide alternative resolving agents for use in chiral separations, inter alia, that do not exhibit the deficiencies commonly associated with charged cyclodextrin mixtures.

SUMMARY OF THE INVENTION

The present invention provides a single-isomer cyclodextrin composition of substantially pure cyclodextrin derivatives having the formula:

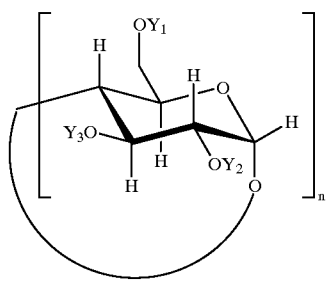

where "n" is 6–12, and at least one of $Y_1$, $Y_2$ and $Y_3$ is $SO_3^-$, and where $Y_1$, $Y_2$ and $Y_3$, being other than $SO_3^-$, are independently hydrogen, a $C_1$–$C_{12}$ alkyl group, a $C_2$–$C_8$ hydroxyalkyl group, a $C_2$–$C_{12}$ acyl group, an aryl group, a carbamate group, a thiocarbamate group or a combination thereof Preferably, the cyclodextrin composition has an isomeric purity of at least 80 mole %, with an isomeric purity of at least 90 mole % being more preferable, and an isomeric purity of at least 95 mole % being even more preferable.

In one embodiment, a single-isomer cyclodextrin composition is provided with $Y_1$ being $SO_3^-$, and $Y_2$ and $Y_3$ being preferably H, $CH_3$, $CH_2CH_3$, $CH_2CHOHCH_3$, $CH_2CN$, or $OCCH_3$. Examples of these single-isomer cyclodextrin derivatives are hepta-6-sulfato-β-cyclodextrin, heptakis-(2,3-diacetyl-6-sulfato)-β-cyclodextrin, heptakis-(2,3-dimethyl-6-sulfato)-β-cyclodextrin, octa-6-sulfato-γ-cyclodextrin, octakis-(2,3-diacetyl-6-sulfato)-γ-cyclodextrin, and octakis-(2,3-dimethyl-6-sulfato)-γ-cyclodextrin.

In another embodiment, a single-isomer cyclodextrin composition is provided with $Y_2$ being $SO_3^-$, and $Y_1$ and $Y_3$ being preferably H, $CH_3$, $CH_2CH_3$, $CH_2CHOHCH_3$, $CH_2CN$, or $OCCH_3$. In other embodiments, the present invention provides single-isomer cyclodextrin compositions with: $Y_3$ being $SO_3^-$ and $Y_1$ and $Y_2$ being preferably H, $CH_3$, $CH_2CHOHCH_3$, $CH_2CN$, or $OCCH_3$; $Y_1$ and $Y_2$ being $SO_3^-$ and $Y_3$ being H, $CH_3$, $CH_2CHOHCH_3$, $CH_2CN$, or $OCCH_3$; $Y_1$ and $Y_3$ being $SO_3^-$ and $Y_2$ being preferably H, $CH_3$, $CH_2CHOHCH_3$, $CH_2CN$, or $OCCH_3$; $Y_2$ and $Y_3$ being $SO_3^-$ and $Y_1$ being preferably H, $CH_3$, $CH_2CHOHCH_3$, $CH_2CN$, or $OCCH_3$.

The present invention also provides a method for electrophorectically separating stereoisomers of a chiral analyte using the above-described single-isomer cyclodextrin compositions. The chiral analyte is separated into its respective stereoisomers by first introducing into an electrophoretic separation chamber a sample of the chiral analyte and of a background electrolyte containing at least one single-isomer cyclodextrin composition and thereafter applying an electric potential across the electrophoretic separation chamber thereby inducing differential migration of the stereoisomers of the chiral analyte.

The present invention provides a method for chromatographically separating stereoisomers of a chiral analyte using the above-described single-isomer cyclodextrin compositions. The chiral analyte is separated into its respective stereoisomers by first introducing into a chromatographic separation chamber the chiral analyte, and a mobile phase containing at least one single-isomer cyclodextrin composition and thereafter applying pressure across the separation chamber thereby inducing differential displacement of the stereoisomers of the chiral analyte.

DETAILED DESCRIPTION OF THE INVENTION

Figure 1:
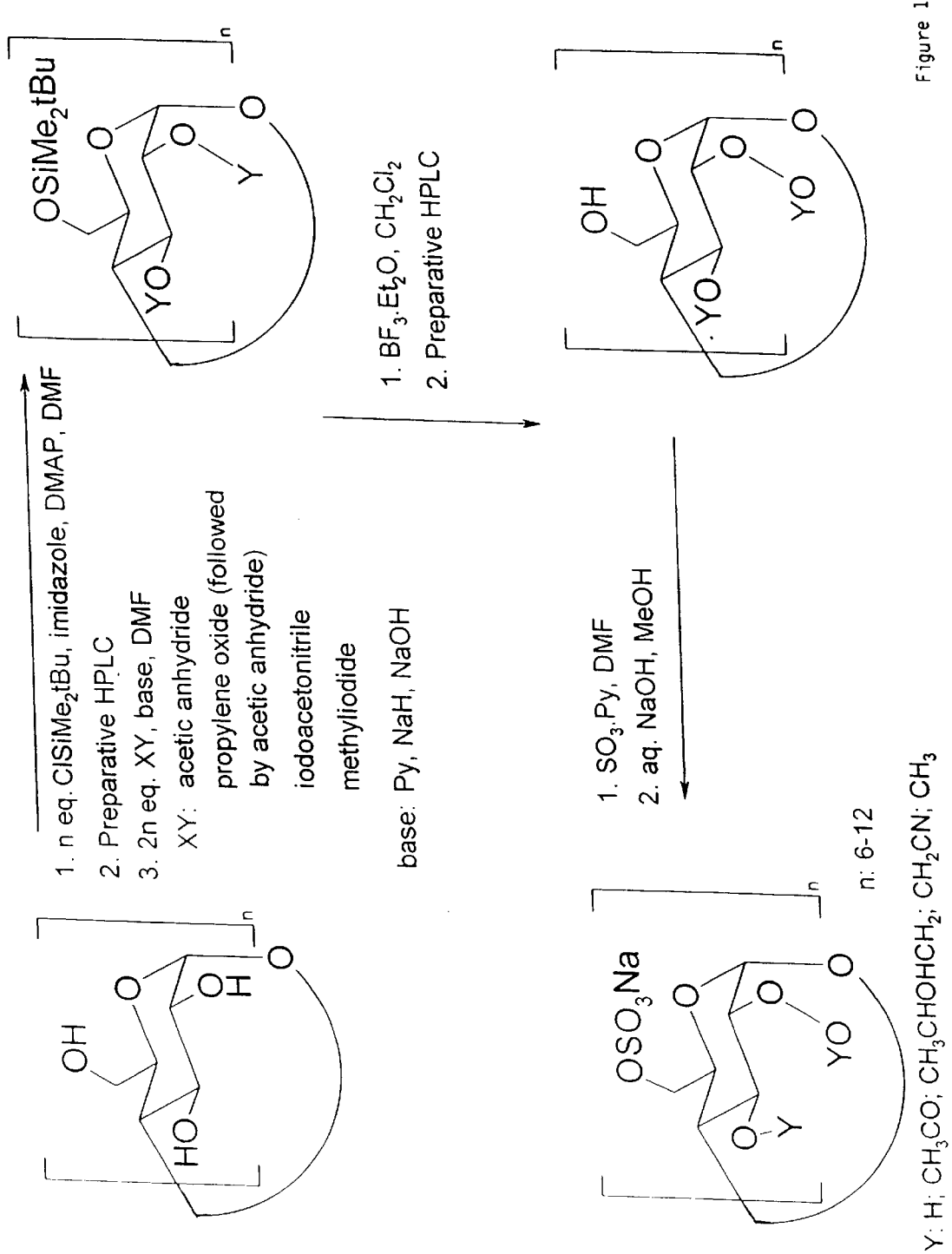
FIG. 1 is a reaction scheme depicting the synthesis of the single isomer 6-sulfato-cyclodextrin derivatives.

The present invention provides a new class of single-isomer charged cyclodextrin derivatives, which are particularly useful as chiral resolving agents in the separation of stereoisomers, and more particulary enantiomers. The single-isomer charged cyclodextrin derivatives of the present invention are substantially pure cyclodextrin derivatives having the formula:

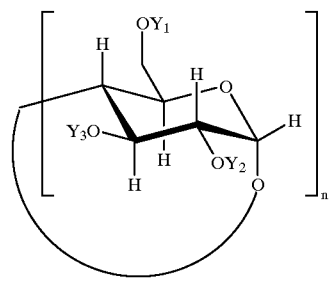

where n is a single integer ranging from 6–12 and at least one of the substituents $Y_1$, $Y_2$ or $Y_3$ is a $SO_3^-$, and $Y_1$, $Y_2$ and $Y_3$, which are other than $SO_3^-$, are hydrogen, a $C_1$–$C_{12}$ alkyl group, a $C_2$–$C_8$ hydroxyalkyl group, a $C_1$–$C_{12}$ alkylnitryl group, a $C_2$–$C_{12}$ acyl group, an aryl group, a carbamate group, a thiocarbamate group or a combination thereof. Advantageously, the functionalized cyclodextrin derivatives of the present invention due to their isomeric purity provide enantiomeric separations, e.g., using electrophoresis, with a consistency and resolution previously not achievable.

In the context of the present invention "substantially pure" means that the majority (i.e., greater than 50 mole %) of the cyclodextrin derivatives present in a given sample are in the form of the target single isomer. Preferably, the cyclodextrin derivatives have an isomeric purity of at least 80 mole %, with at least 90 mole % being more preferred, and at least 95 mole % being even more preferred.

Cyclodextrins to be used in accordance with the present invention are cyclodextrins in which "n", the number of D-(+)-glucopyranose units, is a single integer ranging from 6 to 12. Preferably, the cyclodextrins have a single "n" value from 6 to 9, which are commonly referred to as α-, β-, γ-, and δ-cyclodextrins. Sources of commercially available cyclodextrins include Cerestar (Hammond, Ind.), Wacker GmbH (Munich, Germany), and Cyclolabs (Budapest, Hungary).

In accordance with the present invention, at least one of the substituents $Y_1$, $Y_2$, or $Y_3$ of the glucopyranose unit is a sulfato group, which provides the cyclodextrin derivatives with an ionic charge. Preferably, $Y_1$ is the sulfato group with the remaining non-sulfato $Y_2$ or $Y_3$ substituents being hydrogen, a $C_1$–$C_{12}$ alkyl group, a $C_2$–$C_8$ hydroxyalkyl group, a $C_1$–$C_{12}$ alkylnitryl group, a $C_2$–$C_{12}$ acyl group, an aryl group, a carbamate group, a thiocarbamate group or a mixture thereof. However, if desired, $Y_2$ and $Y_3$ can also be sulfato groups to further increase the ionic charge and/or the binding selectivities of the cyclodextrin derivatives. As will be apparent to those skilled in the art following the teachings of the present invention, the Y substituents can be altered to vary the hydrophobicity or hydrophilicity of the substantially pure single-isomer cyclodextrin derivatives.

The alkyl substituents for $Y_1$, $Y_2$, or $Y_3$ preferably have one to eight carbon atoms, with one to five carbon atoms being preferred. The alkyl chain can be linear, branched, cyclic, saturated, or unsaturated. Examples of alky substituents include, but are not limited to, methyl, ethyl, propyl, isopropyl, n-butyl, sec-butyl or cyclohexyl groups.

The hydroxyalkyl substituents preferably have two to six carbon atoms, with two to four carbon atoms being preferred. The alkyl chain can be linear, branched, cyclic, saturated, or unsaturated. Examples of hydroxyalkyl substituents include, but are not limited to, hydroxyethyl, hydroxypropyl, hydroxybutyl or cyclohexanol groups.

The alkylnitryl substituents preferably have an alkyl chain of one to eight carbon atoms, with one to 5 being more preferred. The alkyl chain can be linear, branched, cyclic, saturated, or unsaturated. Examples of alkylnitryl substituents include, but are not limited to, acetonitryl (i.e., methylcyano), ethylcyano or propylcyano groups.

The acyl substituents preferably have a carbon chain of one to eight carbon atoms, with one to six carbon atoms being more preferred. The carbon chain can be linear, branched, cyclic, saturated, unsaturated or aromatic. Examples of acyl substituents to be used include, but are not limited to, acetyl, propionyl, butyryl, pivaloyl, caproyl or benzoyl groups.

The aryl substituents preferably are monocyclic or bicyclic aromatics, optionally substituted with non-polar alkyl or polar groups. Examples of aryl substituents to be used include, but are not limited to, benzyl or napthenyl groups.

The carbamate and thiocarbamate substituents preferably have alkyl, aryl and substituted aryl groups. Examples of carbamate and thiocarbamate substituents to be used include, but are not limited to, methylcarbamate, ethylcarbamate, methylthiocarbamate, ethylthiocarbamate, phenylcarbamate, phenylthiocarbamate, 3,5-dimethylphenylcarbamate or 3,5-dimethylphenylthiocarbamate.

In one embodiment, the present invention provides substantially pure cyclodextrin derivatives with $Y_1$ (i.e., 6-position) being a sulfato group and $Y_2$ and $Y_3$ (i.e., 2- and 3-positions, respectively) preferably being either hydrogen, a methyl, an acetyl, an acetonitryl or a 2-hydroxypropyl group. In a more preferred embodiment, $Y_2$ and $Y_3$ of the 6-sulfato-cyclodextrin derivatives are the same substituents, thus providing substantially pure per-substituted 6-sulfato-cyclodextrin, 2,3-dimethyl-6-sulfato-cyclodextrin, 2,3-diacetyl-6-sulfato-cyclodextrin, 2,3-diacetonitryl-6-sulfato-cyclodextrin and 2,3-di-(2-hydroxypropyl)-6-sulfato-cyclodextrin. The reaction scheme for synthesizing the 6-sulfato-cyclodextrin derivatives is shown in FIG. 1. For example, to synthesize 2,3-diacetyl-6-sulfato-cyclodextrin, the cyclodextrin starting material is first silylated with t-butyldimethylsilyl chloride using 4-N,N-dimethylamino pyridine as a catalyst, and imidazole as a base. The silylated product is then purified by preparative HPLC. The pure intermediate is allowed to react with acetic anhydride using 4-N,N-dimethylamino pyridine as a catalyst, and pyridine as a base. The crude intermediate is purified by preparative HPLC. The pure acetylated, silylated intermediate is desilylated with borontrifluoride etherate and the crude intermediate is purified by preparative HPLC. The pure intermediate is then reacted with sulfur trioxide.pyridine, then with sodium hydroxide, to obtain the sodium salt of the single-isomer 2,3-diacetyl-6-sulfato-cyclodextrin.

Figure 2:
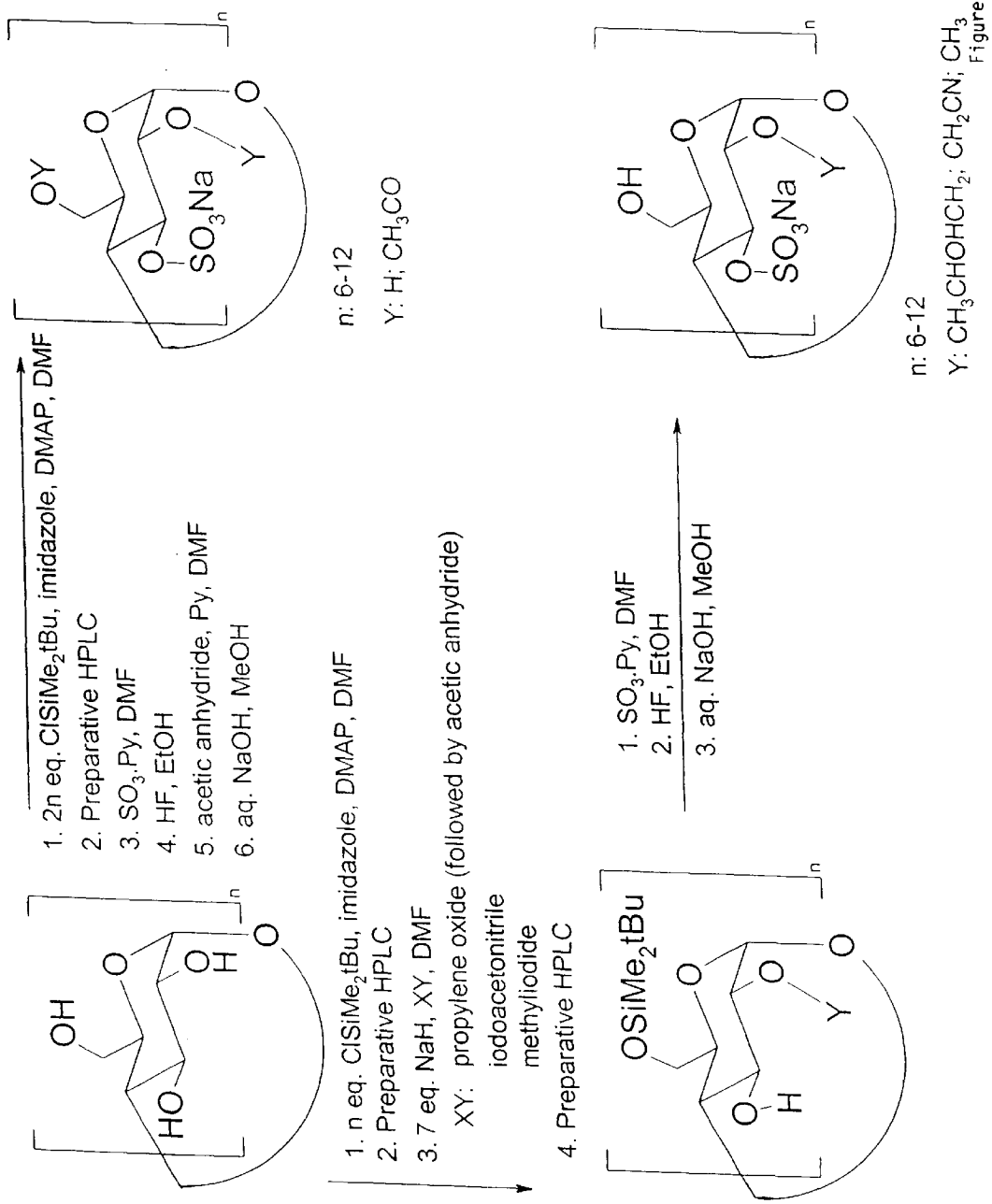
FIG. 2 is a reaction scheme depicting the synthesis of the single isomer 3-sulfato-cyclodextrin derivatives.

In another embodiment, the present invention provides substantially pure cyclodextrin derivatives with $Y_3$ being a sulfato group and $Y_1$ and optionally $Y_2$ preferably being either hydrogen, a methyl, an acetyl, an acetonitryl or a 2-hydroxypropyl group. In a more preferred embodiment, $Y_1$ and $Y_2$ of the 3-sulfato-cyclodextrin derivatives are same substituent, thus providing substantially pure per-substituted 3-sulfato-cyclodextrin, 2,6-dimethyl-3-sulfato-cyclodextrin, 2,6-diacetyl-3-sulfato-cyclodextrin, 2,6-diacetonitryl-3-sulfato-cyclodextrin and 2,6-di-(2-hydroxypropyl)-3-sulfato-cyclodextrin. The reaction schemes for synthesizing 3-sulfato-cyclodextrin and 6-methyl-3-sulfato-cyclodextrin, among others, are shown in FIG. 2. For example, to synthesize 3-sulfato-cyclodextrin, the cyclodextrin starting material is first silylated with t-butyldimethylsilyl chloride using 4-N,N-dimethylamino pyridine as a catalyst, and imidazole as a base. The 2,6-disilylated product is purified by preparative HPLC. The pure intermediate is reacted with sulfur trioxide.pyridine, then with hydrogen fluoride to remove the silyl protecting groups. The desilylated intermediate is reacted with sodium hydroxide to obtain the sodium salt of the 3-sulfato-cyclodextrin. Likewise, to synthesize 6-methyl-3-sulfato-cyclodextrin, the cyclodextrin starting material is first silylated with t-butyldimethylsilyl chloride using 4-N,N-dimethylamino pyridine as a catalyst, and imidazole as a base. The 6-silylated product is purified by preparative HPLC. The pure intermediate is reacted with methyliodide, with sodium hydride as base, to obtain the methylated and silylated crude intermediate. After purification by preparative HPLC, the intermediate is reacted with sulfur trioxide.pyridine, then with hydrogen fluoride to remove the silyl protecting groups. The desilylated intermediate is reacted with sodium hydroxide to obtain the sodium salt of the 6-methyl-3-sulfato-cyclodextrin.

Figure 3:
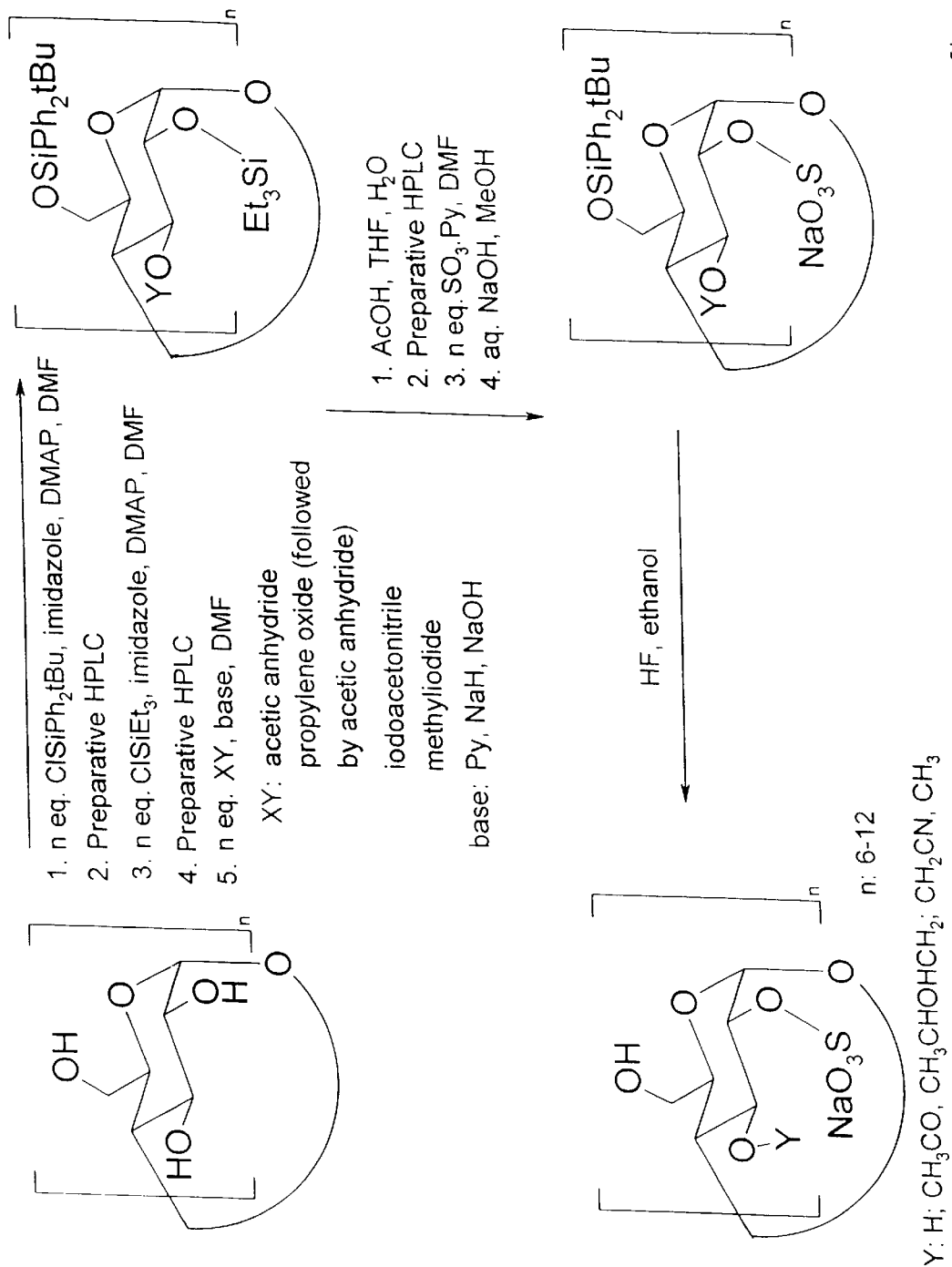
FIG. 3 is a reaction scheme depicting the synthesis of the single-isomer 2-sulfato-cyclodextrin derivatives.

The present invention also provides substantially pure cyclodextrin derivatives with $Y_2$ being a sulfato group, and preferably $Y_1$ being hydrogen and $Y_3$ being either hydrogen, a methyl, an acetyl, an acetonitryl or a 2-hydroxypropyl group. Examples of these 2-sulfato-cyclodextrin derivatives are 2-sulfato-cyclodextrin, 3-methyl-2-sulfato-cyclodextrin, 3-acetyl-2-sulfato-cyclodextrin, 3-acetonitryl-2-sulfato-cyclodextrin and 3-(2-hydroxypropyl)-2-sulfato-cyclodextrin. The reaction scheme for synthesizing these particular single-isomer cyclodextrin derivatives is shown in FIG. 3. For example, to synthesize 3-acetyl-2-sulfato-cyclodextrin, the cyclodextrin starting material is first silylated with t-butyldimethylsilyl chloride using 4-N,N- dimethylamino pyridine as a catalyst, and imidazole as a base. The silylated product is purified by preparative HPLC. The pure intermediate is further reacted with triethylsilyl chloride using 4-N,N-dimethylamino pyridine as a catalyst, and imidazole as a base. The silylated product is purified by preparative HPLC. The pure intermediate then is reacted with acetic anhydride using 4-N,N-dimethylamino pyridine as a catalyst, and pyridine as a base. The crude intermediate is purified by preparative HPLC. The triethylsilyl group is removed from the pure acetylated, silylated intermediate with acetic acid and the new intermediate is purified by preparative HPLC. The purified intermediate is reacted with sulfur trioxide.pyridine, then with HF and sodium hydroxide, to obtain the sodium salt of the single-isomer 3-acetyl-2-sulfato-cyclodextrin.

Figure 4:
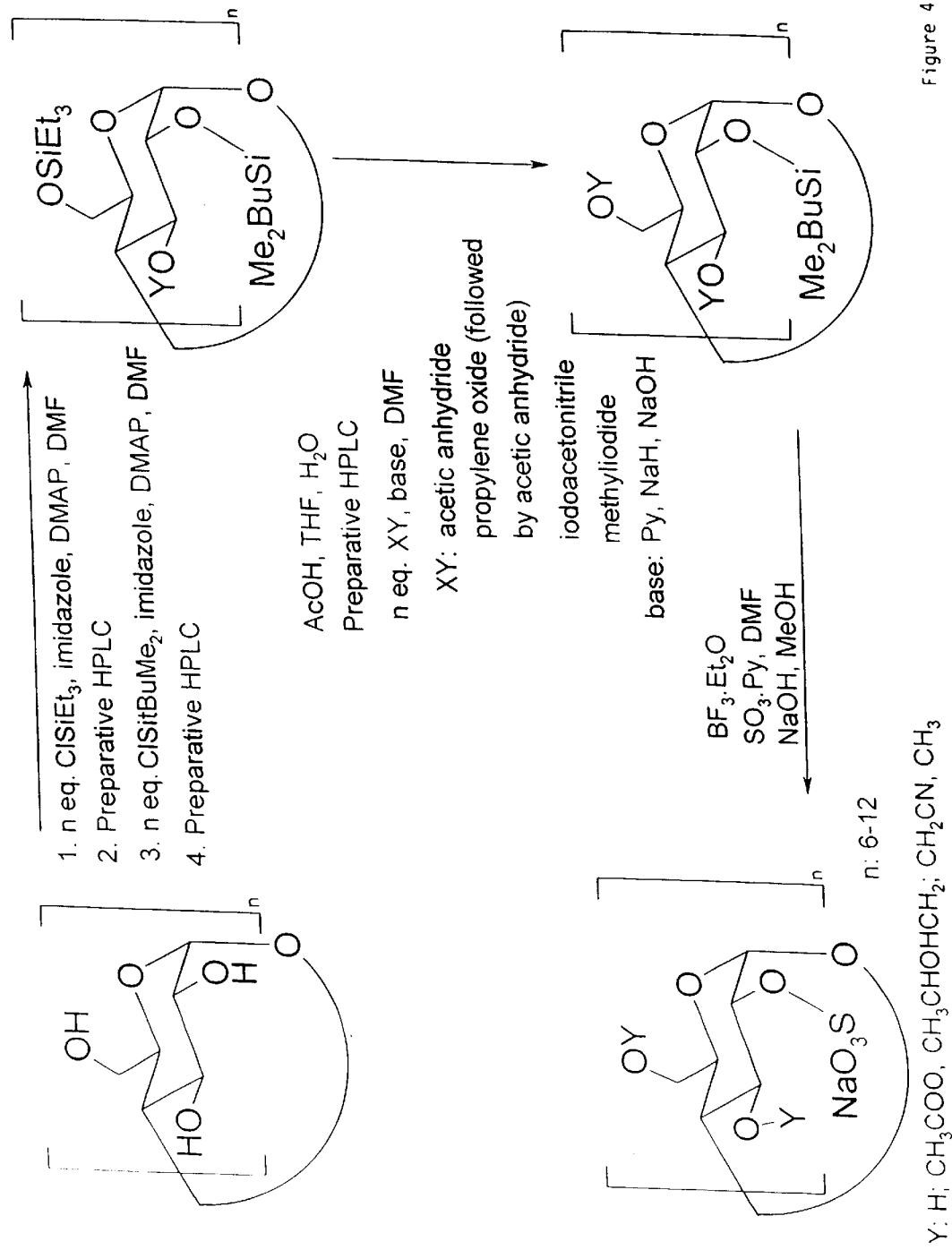
FIG. 4 is an alternative reaction scheme depicting the synthesis of the single-isomer 2-sulfato-cyclodextrin derivatives.

The present invention also provides substantially pure cyclodextrin derivatives with $Y_2$ being a sulfato group, and $Y_1$ and $Y_3$ preferably being either hydrogen, a methyl, an acetyl, an acetonitryl or a 2-hydroxypropyl group. Examples of the per-substituted 2-sulfato-cyclodextrin derivatives are 2-sulfato-cyclodextrin, 3,6-dimethyl-2-sulfato-cyclodextrin, 3,6-diacetyl-2-sulfato-cyclodextrin, 3,6-diacetonitryl-2-sulfato-cyclodextrin and 3,6-di(2-hydroxypropyl)-2-sulfato-cyclodextrin. The reaction scheme for synthesizing these particular single-isomer cyclodextrin derivatives is shown in FIG. 4. For example, to synthesize 3,6-dimethyl-2-sulfato-cyclodextrin, the cyclodextrin starting material is first silylated with triethylsilyl chloride using 4-N,N-dimethylamino pyridine as a catalyst, and imidazole as a base. The silylated product is purified by preparative HPLC. The pure intermediate is reacted with t-butyldimethylsilyl chloride using 4-N,N-dimethylamino pyridine as a catalyst, and imidazole as a base. The silylated product is purified by preparative HPLC. The pure intermediate is then reacted with acetic acid to remove the triethylsilyl protecting groups and the crude intermediate is again purified. The pure 2-silylated intermediate is reacted with methyliodide, with sodium hydride as a base, yielding the crude methylated silylated intermediate which is purified by preparative HPLC. After removal of the t-butyldimethylsilyl protecting groups with HF, and repeated purification by preparative HPLC, the pure final intermediate is reacted with sulfur trioxide pyridine, then with sodium hydroxide, to obtain the sodium salt of the 3,6-dimethyl-2-sulfato-cyclodextrin.

Figure 5:
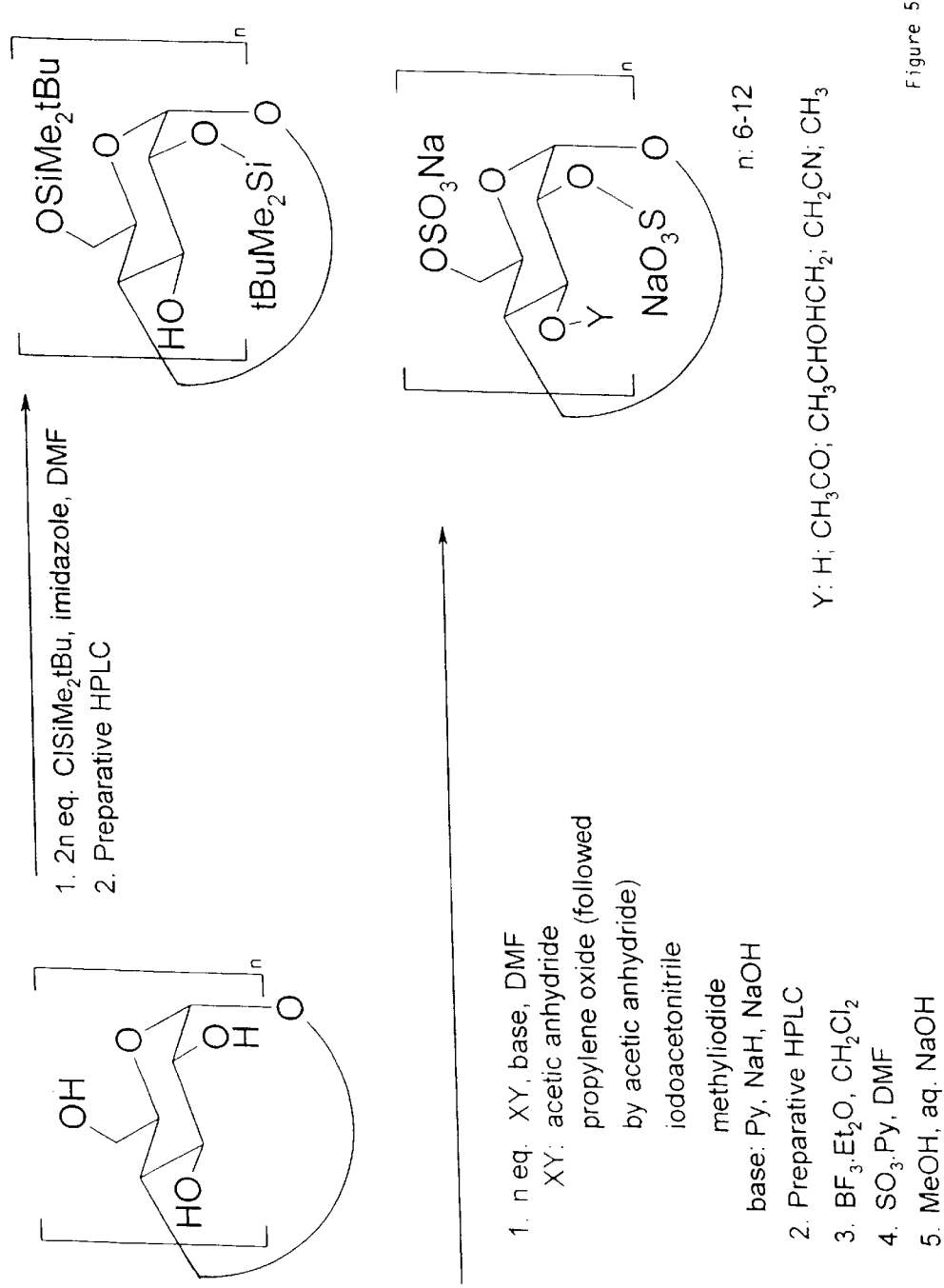
FIG. 5 are reaction schemes depicting the synthesis of the single-isomer 2,6-disulfato-cyclodextrin derivatives.

As described above, more than one of the Y substituents can be a sulfato group. One such embodiment is substantially pure cyclodextrin derivatives with $Y_1$ and $Y_2$ being sulfato groups, and $Y_3$ preferably being either hydrogen, a methyl, an acetyl, an acetonitryl or a 2-hydroxypropyl group. Examples of these cyclodextrin derivatives are 2,6-disulfato-cyclodextrin, 3-methyl-2,6-disulfato-cyclodextrin, 3-acetyl-2,6-disulfato-cyclodextrin, 3-acetonitryl-2,6-disulfato-cyclodextrin and 3-(2-hydroxypropyl)-2,6-sulfato-cyclodextrin. The reaction scheme for synthesizing these particular single-isomer cyclodextrin derivatives is shown in FIG. 5. For example, to synthesize 3-methyl-2,6-disulfato cyclodextrin, the cyclodextrin starting material is first silylated with t-butyldimethylsilyl chloride using 4-N,N-dimethylamino pyridine as a catalyst, and imidazole as a base. The silylated product is purified by preparative HPLC. The pure intermediate is then reacted with methyliodide, with sodium hydride as base, yielding the crude methylated silylated intermediate which is purified by preparative HPLC. After removal of the t-butyldimethylsilyl protecting groups with HF, and repeated purification, the pure final intermediate is further reacted with sulfur trioxide.pyridine, then with sodium hydroxide, to obtain the sodium salt of the 3-methyl-2,6-disulfato cyclodextrin.

Figure 6:
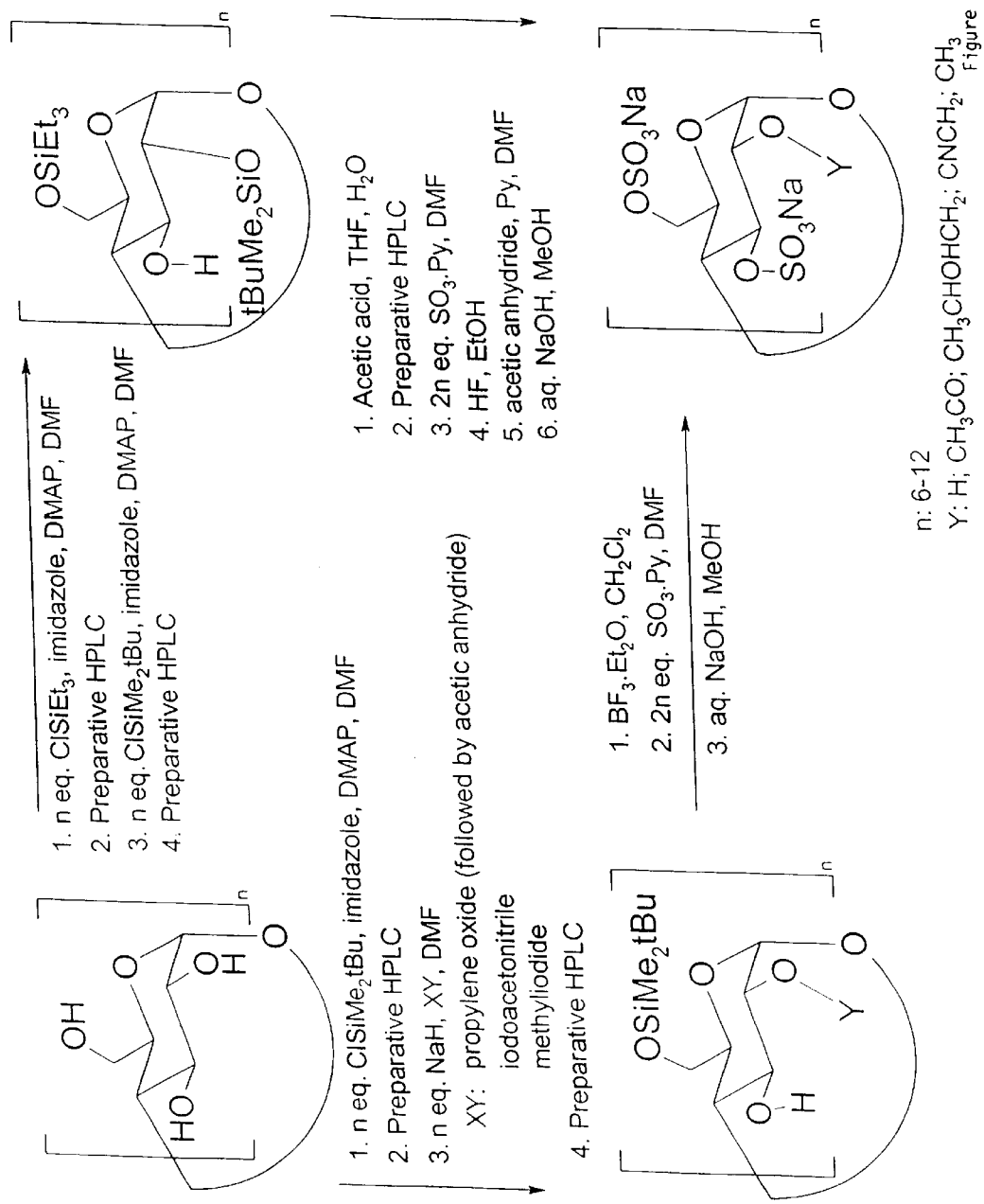
FIG. 6 is a reaction scheme depicting the synthesis of the single-isomer 3,6-disulfato-cyclodextrin derivatives.

The present invention also provides substantially pure cyclodextrin derivatives with $Y_1$ and $Y_3$ being sulfato groups, and $Y_2$ preferably being either hydrogen, a methyl, an acetyl, an acetonitryl or a 2-hydroxypropyl group. Examples of these cyclodextrin derivatives are 3,6-disulfato-cyclodextrin, 2-methyl-3,6-disulfato-cyclodextrin, 2-acetyl-3,6-disulfato-cyclodextrin, 2-acetonitryl-3,6-disulfato-cyclodextrin and 2-(2-hydroxypropyl)-3,6-sulfato-cyclodextrin. The reaction scheme for synthesizing these particular single-isomer cyclodextrin derivatives is shown in FIG. 6. For example, to synthesize 3,6-disulfato cyclodextrin, the cyclodextrin starting material is first silylated with triethylsilyl chloride using 4-N,N-dimethylamino pyridine as a catalyst, and imidazole as base. The silylated product is then purified with preparative HPLC. The pure intermediate is further reacted with t-butyldimethylsilyl chloride using 4-N,N-dimethylamino pyridine as a catalyst, and imidazole as a base, and purified by HPLC. The pure intermediate then is reacted with acetic acid to remove the triethylsilyl protecting groups and the crude intermediate again is purified. The pure 2-silylated intermediate is reacted with sulfur trioxide.pyridine, then with HF, then with sodium hydroxide, to obtain the sodium salt of 3,6-disulfato-cyclodextrin.

The single-isomer charged cyclodextrin derivatives of the present invention are particularly useful as chiral resolving agents for the separation of enantiomers via conventional separation techniques such as high pressure liquid chromatography and electrophoresis. As will be apparent to those skilled in the art, the single-isomer cyclodextrin derivatives of the present invention are also useful for other applications, in which cyclodextrins are typically used.

Enantiomers to be separated using the cyclodextrin derivatives of the present invention include neutral, basic, acidic and zwitterionic analytes. Protocols for using cyclodextrins as resolving agents in electrophoresis or high pressure liquid chromatography are well known in the art. For example, according to the charged resolving agent migration model (Williams et al. *J. Chromatogr. A*. 776 (1997) 295), in capillary electrophoresis, the charged single-isomer cyclodextrin derivative is added to both a low pH (e.g., pH 2.2) or a high pH (e.g., pH 9.5) buffer to obtain background electrolytes (BE). The electrode vials and the separation chamber of the electrophoretic system are then filled with the background electrolyte. The sample containing the enantiomers to be separated is dissolved in the background electrolytes, and an aliquot of this solution is injected into the separation chamber. The separation potential is applied to move the analytes past the detector of the electrophoretic unit. Due to the differential interactions of the enantioners with the single-isomer charged cyclodextrins which alter their electrophoretic mobilities, the enantiomers arrive at the detector at different times, thus resulting in their separation.

The following non-limiting examples illustrate the synthesis of the single-isomer charged cyclodextrin derivatives of the present invention and their use as resolving agents in electrophoresis applications.

EXAMPLES

Example 1

Synthesis of Heptakis-(2,3-diacetyl-6-sulfato)-β-cyclodextrin

Figure 7:
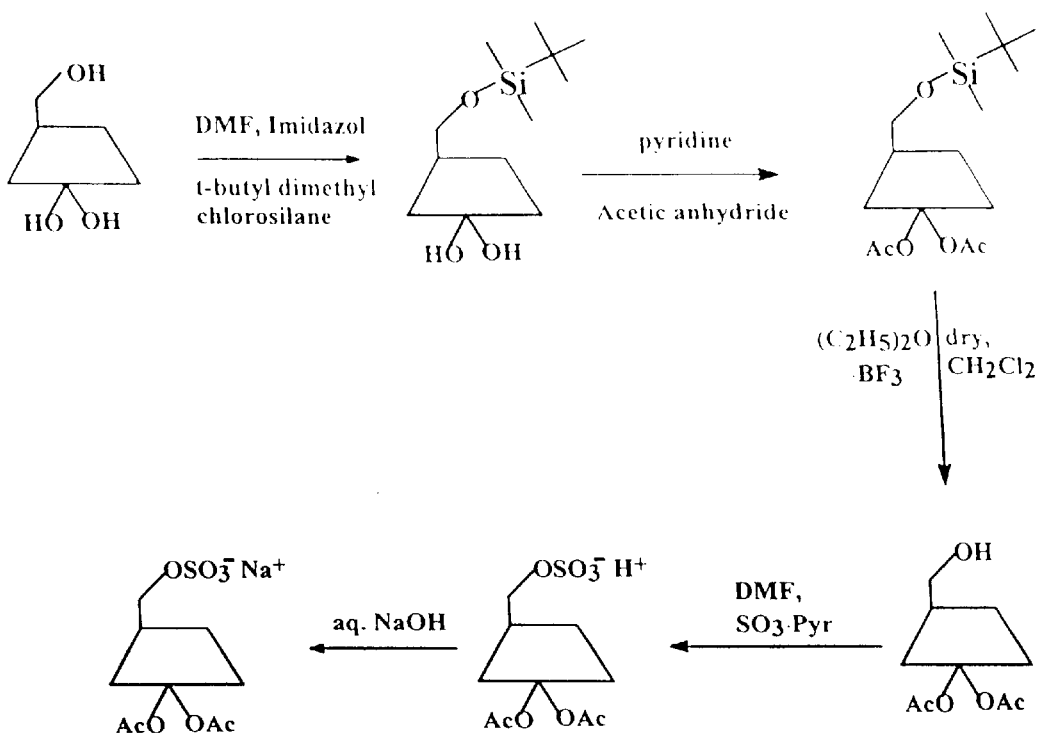
FIG. 7 is a reaction scheme depicting the synthesis of the single-isomer heptakis-(2,3-diacetyl-6-sulfato)-β-cyclodextrin.

Heptakis-(2,3-diacetyl-6-sulfato)-β-cyclodextrin was prepared following the reaction scheme shown in FIG. 7. All chemicals for the synthesis were obtained from Aldrich Chemical Company (Milwaukee, Wis., USA), except 13-cyclodextrin, which was obtained from Cerestar (Hammond, Ind., USA). Heptakis-(2,3-diacetyl-6-sulfato)-β-cyclodextrin was produced by first reacting β-cyclodextrin with t-butyldimethylsilyl chloride as described in Takeo et al., *Carbohydr. Res.* 1989, 187, 203, which is incorporated herein by reference. Briefly, 79 mmol imidazole and 7.9 mmol 4-N,N-dimethylamino pyridine were added to warm N,N-dimethylformamide, followed by 8.8 mmol dried β-cyclodextrin. 66 mmol t-butyldimethylsilyl chloride was dissolved in ethyl acetate and dropped into the β-cyclodextrin solution. Once the reaction was complete, excess t-butyldimethylsilyl chloride was quenched by the addition of methanol, the reaction mixture was poured into an HCl solution to protonate the excess imidazole and precipitate the silylated cyclodextrin. The crude product, dissolved in hexanes, was purified by preparative gradient elution column chromatography (HPLC) using the equipment set forth in Vigh et al., *J. Chromatogr.* 1989, 484, 237, incorporated herein by reference, a 50 mm I.D., 300 mm long preparative HPLC column packed with 30 nm pore size, 10 μm irregular silica (Merck, Darmstadt, Germany), and hexane:ethylacetate:ethanol as eluent as described in Takeo et al. The purified intermediate was then peracetylated with acetic anhydride as described in Takeo et al. Specifically, to 200 mL of dry pyridine was added 0.5 mmol 4-N,N-dimethylamino pyridine, 5 mmol silylated cyclodextrin intermediate and 17 mL acetic anhydride. The reaction mixture was heated for 20 hours at 90° C., then quenched in water; the crude precipitate was collected and again was purified by gradient elution preparative column chromatography on silica gel using hexane: ethylacetate: ethanol as eluent as previously described.

The purified heptakis-(2,3-diacetyl-6-t-butylsilyl-dimethyl)-β-cyclodextrin was then reacted with boron trifluoride etherate as described in Takeo et al. to remove the dimethyl-t-butylsilyl protecting groups. Specifically, 4 mmol of the acetylated silylated intermediate was added to 225 mL dry dichloromethane and 10 mL boron trifluoride etherate. After 3 hours, the reaction mixture was quenched with water, neutralized with sodium carbonate, the organic phase was repeatedly washed with water and the organic phase was evaporated to dryness. The crude product was repurified by gradient elution preparative column chromatography on silica gel using hexane:ethylacetate:ethanol as eluent, as described above. Finally, the purified heptakis-(2,3-diacetyl)-β-cyclodextrin was reacted with $SO_3$·pyridine in DMF as described in U.S. Pat. No. 4,020,160 to Bernstein et al., incorporated herein by reference, to completely sulfate the primary hydroxyl groups of the cyclodextrin. Specifically, to 200 mL dry N,N-dimethylformamide, was added 5 mL dry pyridine and 6 mmol purified heptakis-(2,3-diacetyl)-cyclodextrin, followed by 10 g $SO_3$·pyridine. Progress of the reaction was monitored by indirect UV-detection capillary electrophoresis as set forth in Nardi et al, *Electrophoresis* 1990, 11, 774, incorporated herein by reference, using a 20 mM p-toluenesulfonic acid background electrolyte, whose pH was adjusted to 8 with tris (hydroxymethyl)aminomethane.

Figure 8:
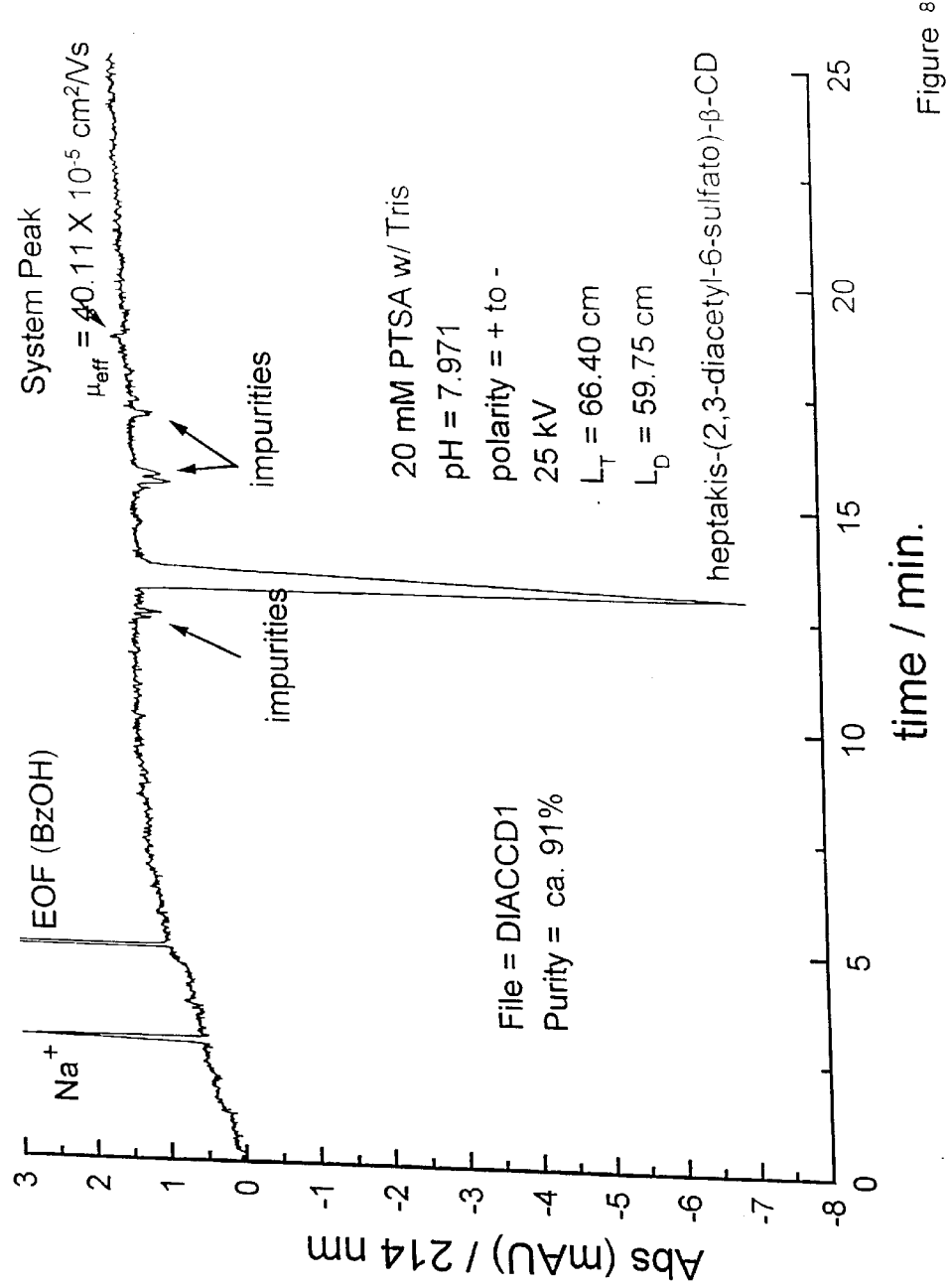
FIG. 8 is an indirect UV-detection electropherogram of the single-isomer heptakis-(2,3-diacetyl-6-sulfato)-β-cyclodextrin.

Once complete, the reaction mixture was poured into acetone, the semi-solid material was filtered out and redissolved in water. The aqueous solution was neutralized with NaOH and the material was reprecipitated with ethanol. The solid material was filtered out, redissolved in water and the remaining sodium sulfate was removed by repeated addition of ethanol. Finally, the end product was dried in a vacuum oven at 80° C. to afford pure heptakis-(2,3-diacetyl-6-sulfato)-β-cyclodextrin. The purity of the material was checked by indirect UV detection capillary electrophoresis as described above and calculated to be greater than 90 mole %. The electropherogram of the heptakis-(2,3-diacetyl-6-sulfato)-β-cyclodextrin sample is shown in FIG. 8.

Figure 9:
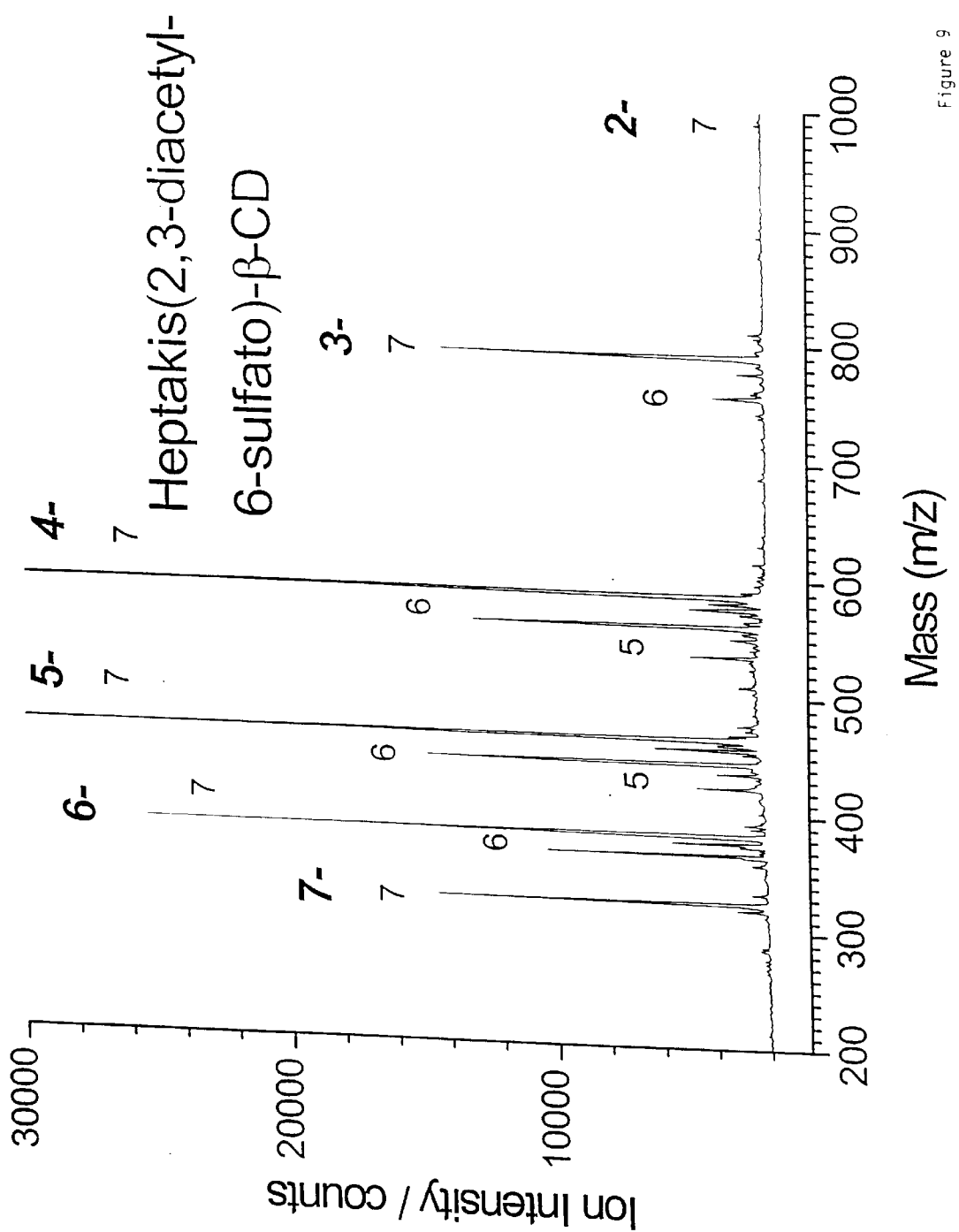
FIG. 9 is an electrospray-ionization mass spectrum of the single-isomer heptakis-(2,3-diacetyl-6-sulfato)-β-cyclodextrin.

Electrospray ionization mass spectra were also obtained with a Vestec model 201-A single quadrupole mass spectrometer, which was equipped with the Vestec electrospray ion source (PerSeptive Biosystems, Vestec Products, Framingham, Mass.). Heptakis-(2,3-diacetyl-6-sulfato)-β-cyclodextrin was dissolved in 75 25% (v/v) mixture of methanol water at a concentration of 4 mg/mL. The apparent pH of the sample solution, measured with a combination glass electrode calibrated with aqueous reference buffers, was 6.6. The heptakis-(2,3-diacetyl-6-sulfato)-β-cyclodextrin solution was introduced by a model 341B SAGE syringe pump (Orion Research, Boston, Mass.) via a Valco injector with a 1 μL internal loop (Valco, Houston, Tex.). The solution was loaded into the loop of the sampling valve and introduced into the ion source at a flow rate of 1.6 μL/min. The ion source block and the spray chamber were maintained at 250° C. and 50° C., respectively. Voltages on the needle, nozzle and collimator of the electrospray ion source were set at −2.4 kV, −0.2 kV and −10 V, respectively. The skimmer potential was −10 V generating a skimmer-collimator voltage bias value of 0 V. The mass range was limited to m/z 1100 and an average of five scans were taken. The electrospray-ionization mass spectrum is shown in FIG. 9.

Example 2

Synthesis of Heptakis-6-sulfato-β-cyclodextrin

Figure 10:
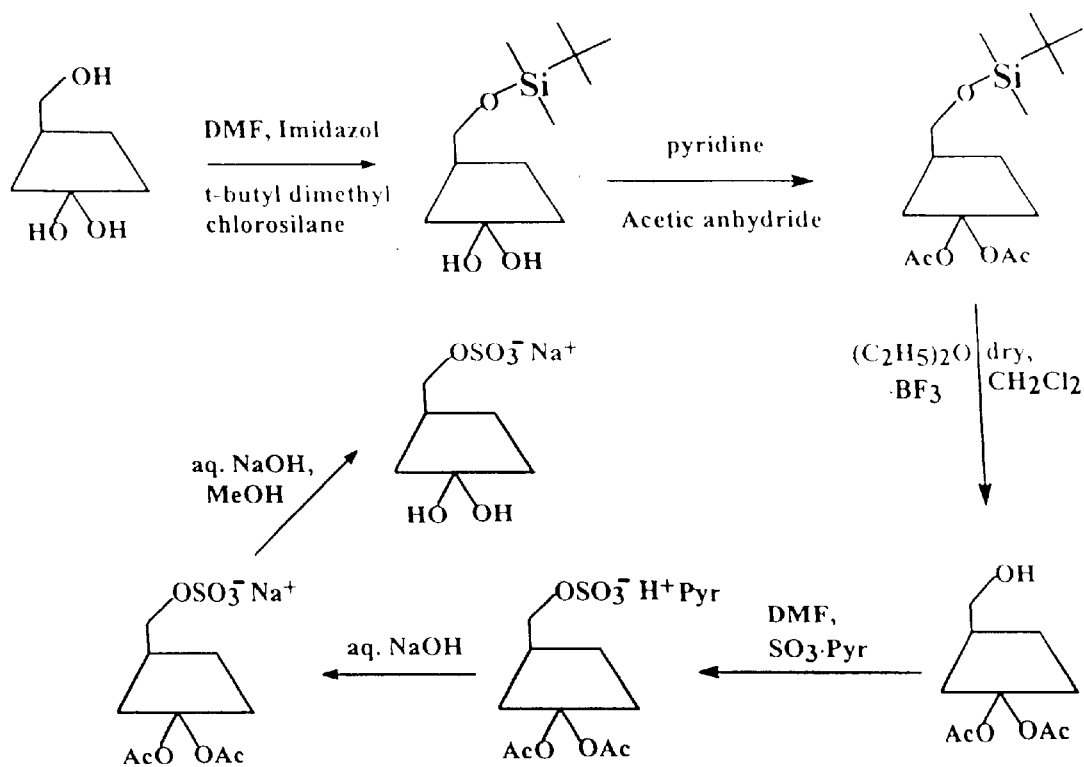
FIG. 10 is a reaction scheme depicting the synthesis of the single-isomer hepta-6-sulfato-β-cyclodextrin.
Figure 11:
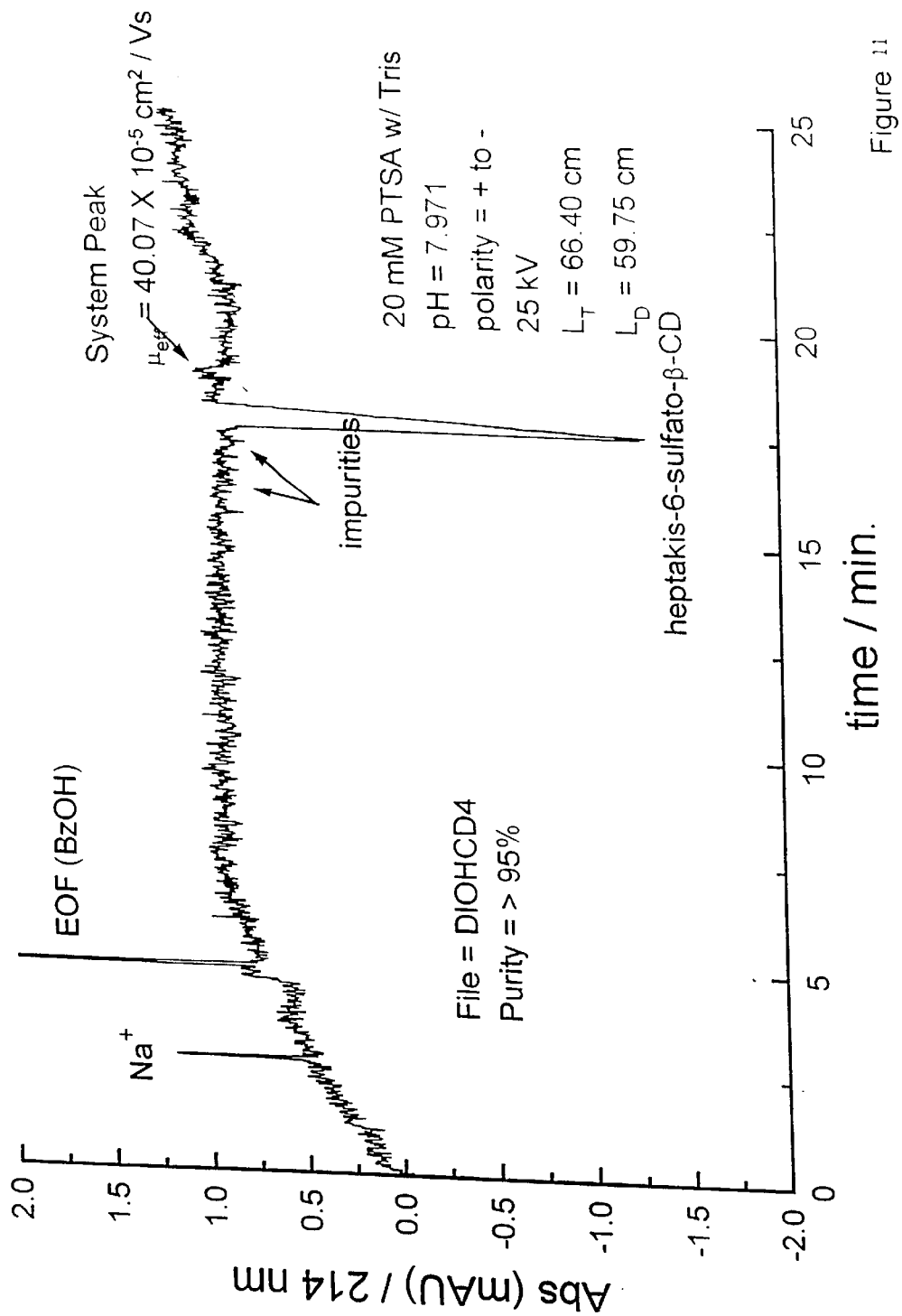
FIG. 11 is an indirect UV-detection electropherogram of the single-isomer hepta-6-sulfato-β-cyclodextrin.
Figure 12:
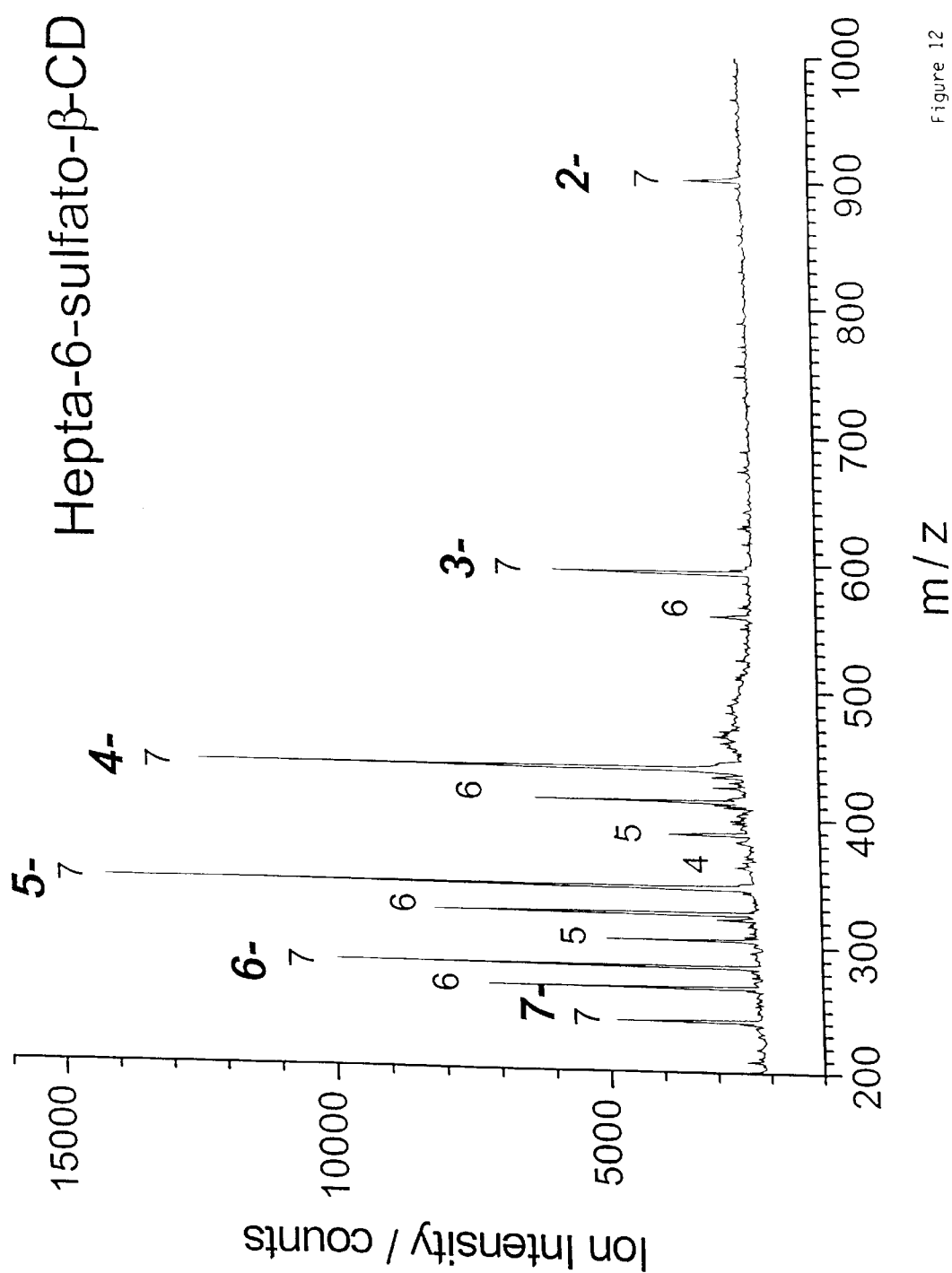
FIG. 12 is an electrospray-ionization mass spectrum of the single-isomer hepta-6-sulfato-β-cyclodextrin.

Substantially pure hepta-6-sulfato-β-cyclodextrin was prepared following the reaction scheme shown in FIG. 10. Briefly, heptakis-(2,3-diacetyl-6-sulfato)-β-cyclodextrin prepared as in Example 1 was deacetylated by dissolving 4 mmol heptakis-(2,3-diacetyl-6-sulfato)-β-cyclodextrin in 125 mL 50° C. water, adding 6 mL of 10 M aqueous NaOH to the solution, then adding, slowly, 5 mL methanol and stirring the mixture for 12 hours. Once indirect UV detection CE indicated that the reaction was complete following the procedure of Example 1, the reaction mixture was poured into ethanol, the solid was collected by filtration, washed with ethanol and dried in a vacuum oven at 80° C. yielding the end product, heptakis-6-sulfato-β-cyclodextrin. The purity of the final product was determined by indirect UV detection CE using 20 mM p-toluenesulfonic acid (PTSA) as a background electrolyte (BE), whose pH was adjusted to 8 with tris(hydroxymethyl)aminomethane (TRIS), and calculated to be greater than 95 mole %. The electropherogram of the heptakis-6-sulfato-β-cyclodextrin sample is shown in FIG. 11. An electrospray-ionization mass spectrum of the final product is shown in FIG. 12.

Example 3

Synthesis of Heptakis-(2,3-dimethyl-6-sulfato)-β-cyclodextrin

Figure 13:
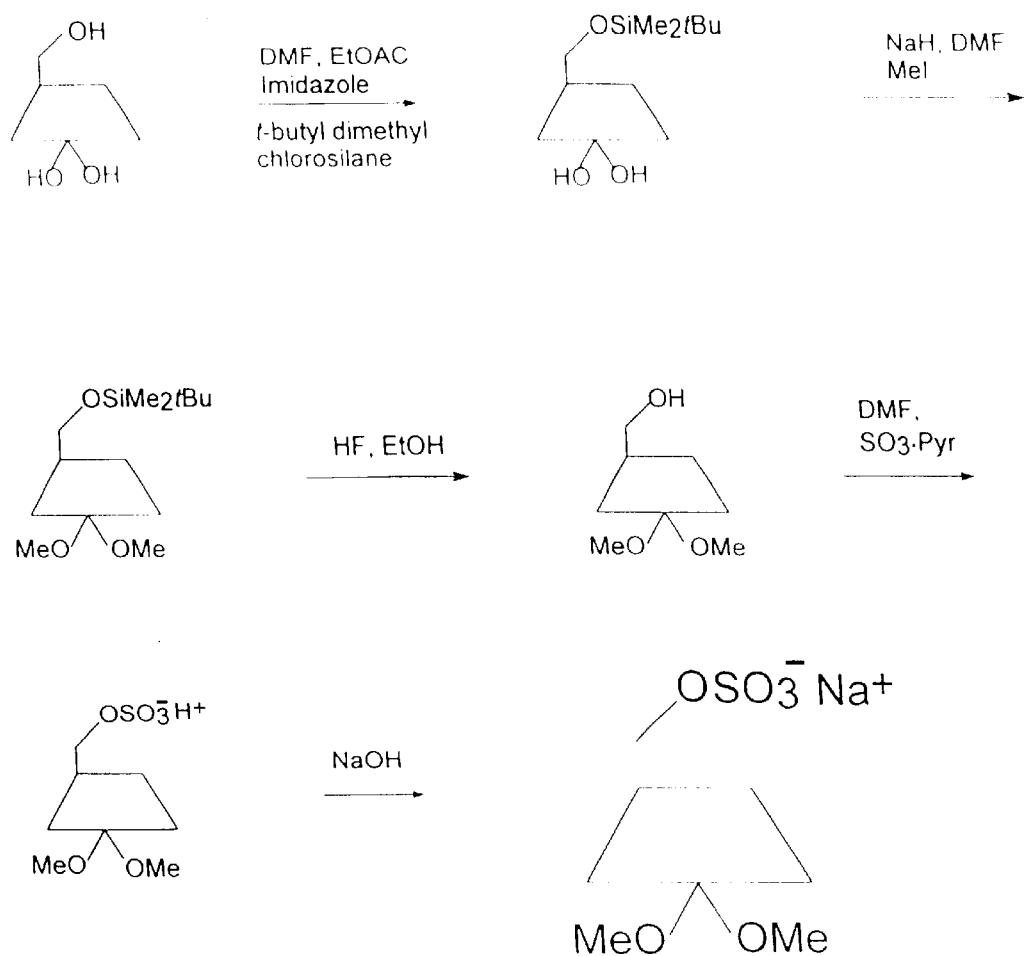
FIG. 13 is a reaction scheme depicting the synthesis of the single-isomer heptakis-(2,3-dimethyl-6-sulfato)-β-cyclodextrin.

The sodium salt of heptakis-(2,3-dimethyl-6-sulfato)-β-cyclodextrin was prepared following the reaction scheme shown in FIG. 13. First, heptakis-6-t-butyldimethylsilyl-β-cyclodextrin was obtained by reacting β-cyclodextrin with t-butyldimethylsilyl chloride as described in Example 1. The raw reaction mixture was purified by preparative gradient elution column chromatography using a silica gel column and the n-hexane: ethyl acetate: ethanol eluent system as described in Example 1.

The pure intermediate was methylated with iodomethane in the presence of NaH and purified as described in Takeo et al. Specifically, 220 mL anhydrous tetrahydrofuran and 5 g NaH were added to a freshly flamed three-neck flask. A mixture of 7 mmol heptakis-6-t-butyldimethylsilyl-β-cyclodextrin, 35 mL methyliodide and 30 mL anhydrous tetrahydrofuran was added, dropwise, to the cool flask, allowed to react overnight, and was finally quenched with ethanol and mixed with butylacetate. The NaI precipitate was filtered off and the solvents were removed on a rotavap. The crude reaction mixture was extensively purified by preparative gradient elution column chromatography using the n-hexane:ethyl acetate:ethanol eluent system as in Example 1. 200 mL ethanol and 12 mmol of this second methylated, silylated cyclodextrin intermediate were added to a polyethylene beaker and reacted with 37 mL HF overnight, as described in Vigh et al., to remove the t-butyldimethylsilyl protecting group. The excess HF was carefully neutralized with $NaHCO_3$ and the inorganic components were removed from the reaction mixture by filtration. After removal of the alcohol-water solvent mixture on a rotavap, the crude reaction mixture containing heptakis-(2,3-dimethyl)-β-cyclodextrin was once again repurified by preparative gradient elution column chromatography using the n-hexane:ethyl acetate:ethanol eluent system as in Example 1.

The pure third intermediate was then sulfated with $SO_3$·pyridine as described in Example 1, but with N,N'-dimethylformamide as the solvent. The completeness of the sulfation reaction was monitored by indirect UV-detection CE using a 20 mM p-toluenesulfonic acid (PTSA) background electrolyte, whose pH was adjusted to 8 with tris (hydroxymethyl)aminomethane (TRIS).

Figure 14:
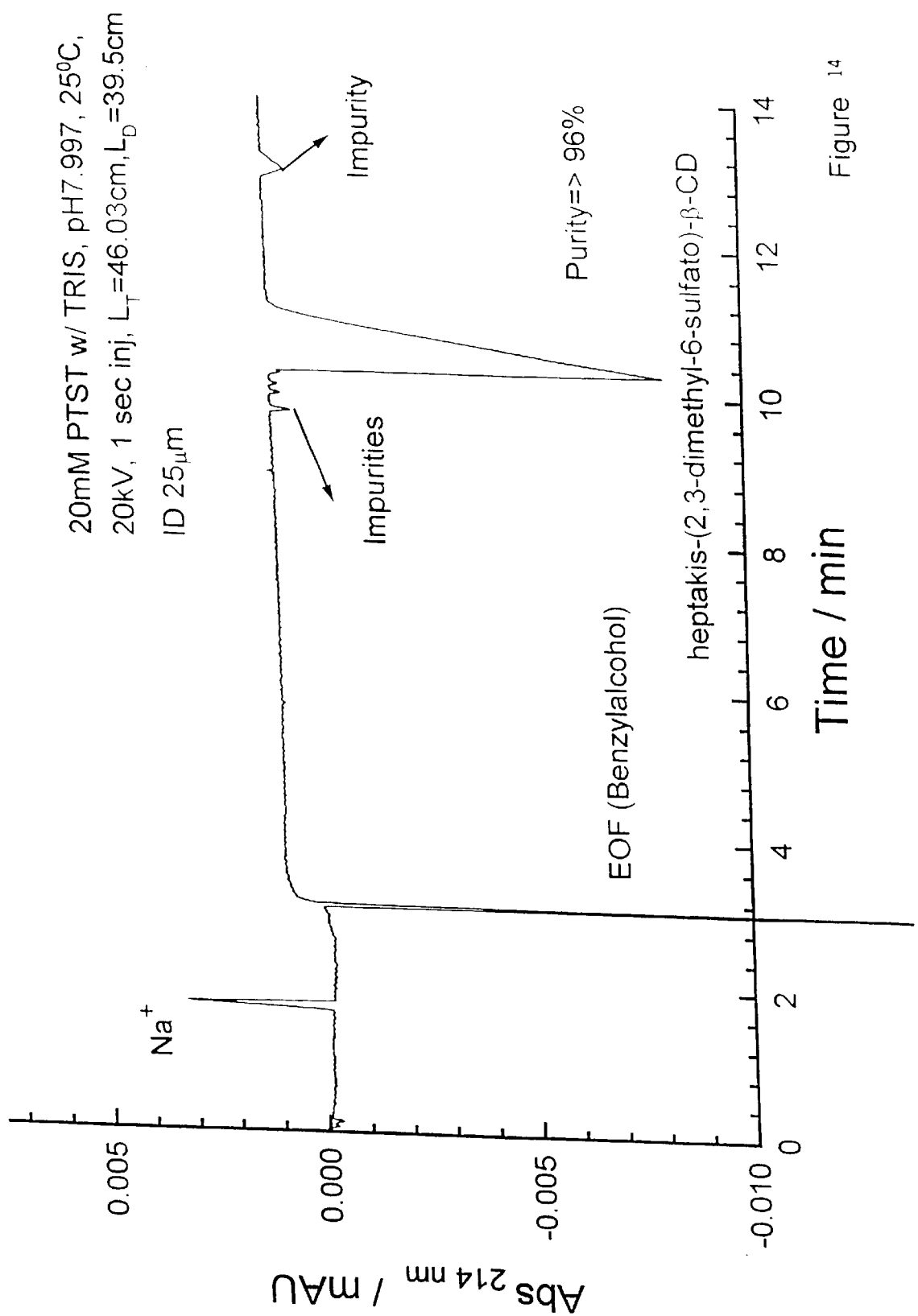
FIG. 14 is an indirect UV-detection electropherogram of the single-isomer heptakis-(2,3-dimethyl-6-sulfato)-β-cyclodextrin.
Figure 15:
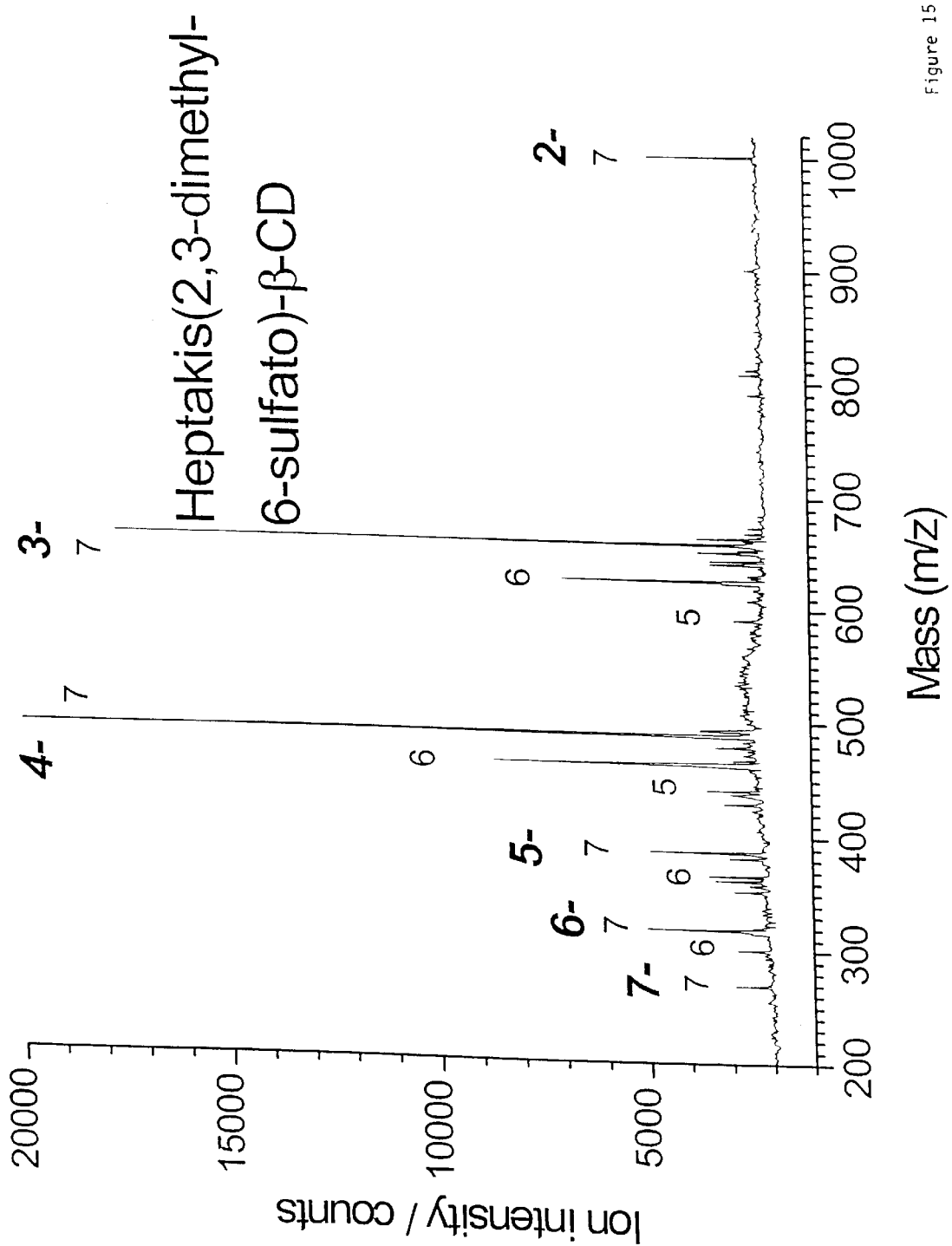
FIG. 15 is an electrospray-ionization mass spectrum of the single-isomer heptakis-(2,3-dimethyl-6-sulfato)-β-cyclodextrin.

Once the sulfation reaction was complete, the reaction mixture was poured into a tenfold excess of acetone, the gummy product was separated, redissolved in water and reacted with NaOH to liberate pyridine. The sodium sulfate byproduct was removed by repeated partial precipitation using ethanol. Finally, pure heptakis-(2,3-dimethyl-6-sulfato)-β-cyclodextrin was obtained by pouring the sodium sulfate-free aqueous solution into excess ethanol, collecting the precipitate and carefully drying it in the vacuum oven overnight. An indirect UV-detection electropherogram of the heptakis-(2,3-dimethyl-6-sulfato)-β-cyclodextrin sample is shown in FIG. 14, in which purity was calculated to be greater than 96 mole %. An electrospray-ionization mass spectrum of the heptakis-(2,3-dimethyl-6-sulfato)-β-cyclodextrin sample is shown in FIG. 15.

Example 4
Electrophoretic Separations using Heptakis-(2,3-diacetyl-6-sulfato)-β-cyclodextrin Two buffer stock solutions (a low pH buffer (pH 2.5) and a high pH buffer (pH 9.5)) were prepared according to the requirements of the charged resolving agent migration model (CHARM model) of CE enantiomer separations as described in Williams, B. A.; Vigh, Gy. *J. Chromatogr.* 1997, 776, 295, which is herein incorporated by reference. The low pH buffer was prepared by adding 0.0250 mole of concentrated (85% w/w) phosphoric acid to enough deionized water (Milli-Q, Millipore, Milford, Mass., USA) to obtain a solution of about 0.95 L. This solution was titrated to pH=2.5 with a saturated aqueous solution of LiOH using a combination glass electrode and a precision pH meter (both of them from Corning Science Products, Corning, N.Y., USA). Finally, the solution was quantitatively transferred to a 1 L volumetric flask, the volume was brought to mark with deionized water and the pH was remeasured. The high pH buffer was prepared similarly, except that 0.0250 mole of ethanolamine was titrated to pH=9.5 with an aqueous solution of methansulfonic acid, quantitatively transferred to a 1 L volumetric flask, the volume was brought to mark with deionized water and the pH was remeasured.

5, 10, 15, 30 and 50 mM heptakis-(2,3-diacetyl-6-sulfato)-β-cyclodextrin (HDAS-βCD) low pH and high pH background electrolytes (BE) were prepared by weighing out the required amounts of the sodium salt of heptakis-(2,3-diacetyl-6-sulfato)-β-cyclodextrin into 25 mL volumetric flasks and bringing the volumes to mark with the low pH and the high pH buffer stock solutions, respectively. 250 μL samples of three racemic analytes (α-methyl-(α-phenyl-succinimide (a neutral analyte), chlophedianol (a basic analyte), ciprofibrate (an acidic analyte)) were prepared at 0.5 mM concentrations in the P/ACE microvials with the respective HDAS-μCD BEs.

Separations were carried out on a UV detector-equipped P/ACE 2100 CE unit operated under the Gold Ver. 8.01 systems software (Beckman Instruments, Fullerton, Calif., USA). The detection wavelength was set at 214 nm, the cartridge coolant was thermostated at 20° C. The separations were carried out in 25 μm i.d. untreated fused silica capillaries (Polymicro Technologies, Phoenix, Ariz., USA) with a 45 cm total length and a 39 cm injector-to-detector length. The injection pressure was set at 5 p.s.i, the injection time was 1 second. The applied potential was varied between 12 kV and 20 kV in order to maintain a power dissipation of 500 to 700 mW/m.

Figure 16:
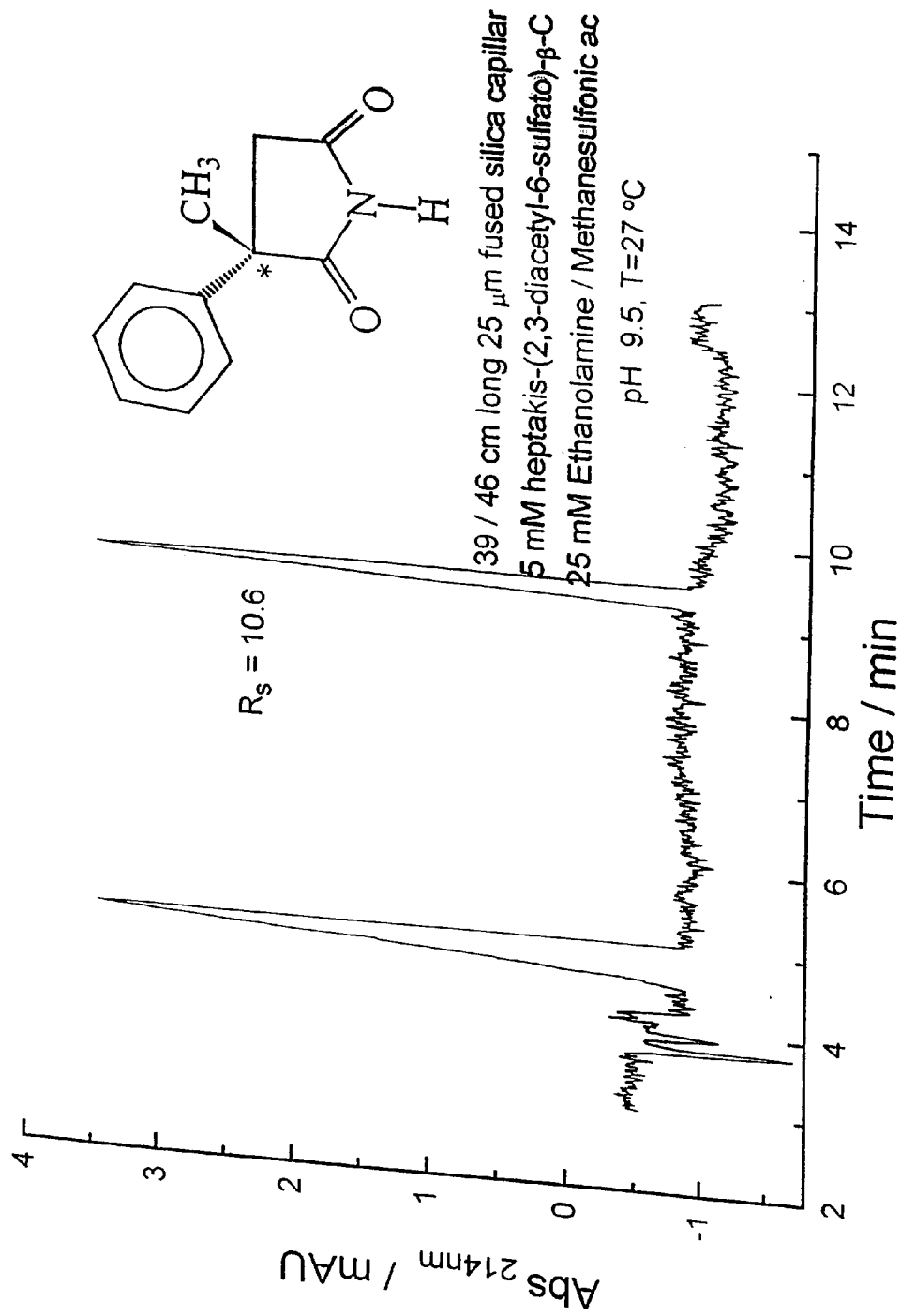
FIG. 16 is an electropherogram of racemic α-methyl-α-phenyl-succinimide separated with the single-isomer heptakis-(2,3-diacetyl-6-sulfato)-β-cyclodextrin.
Figure 17:
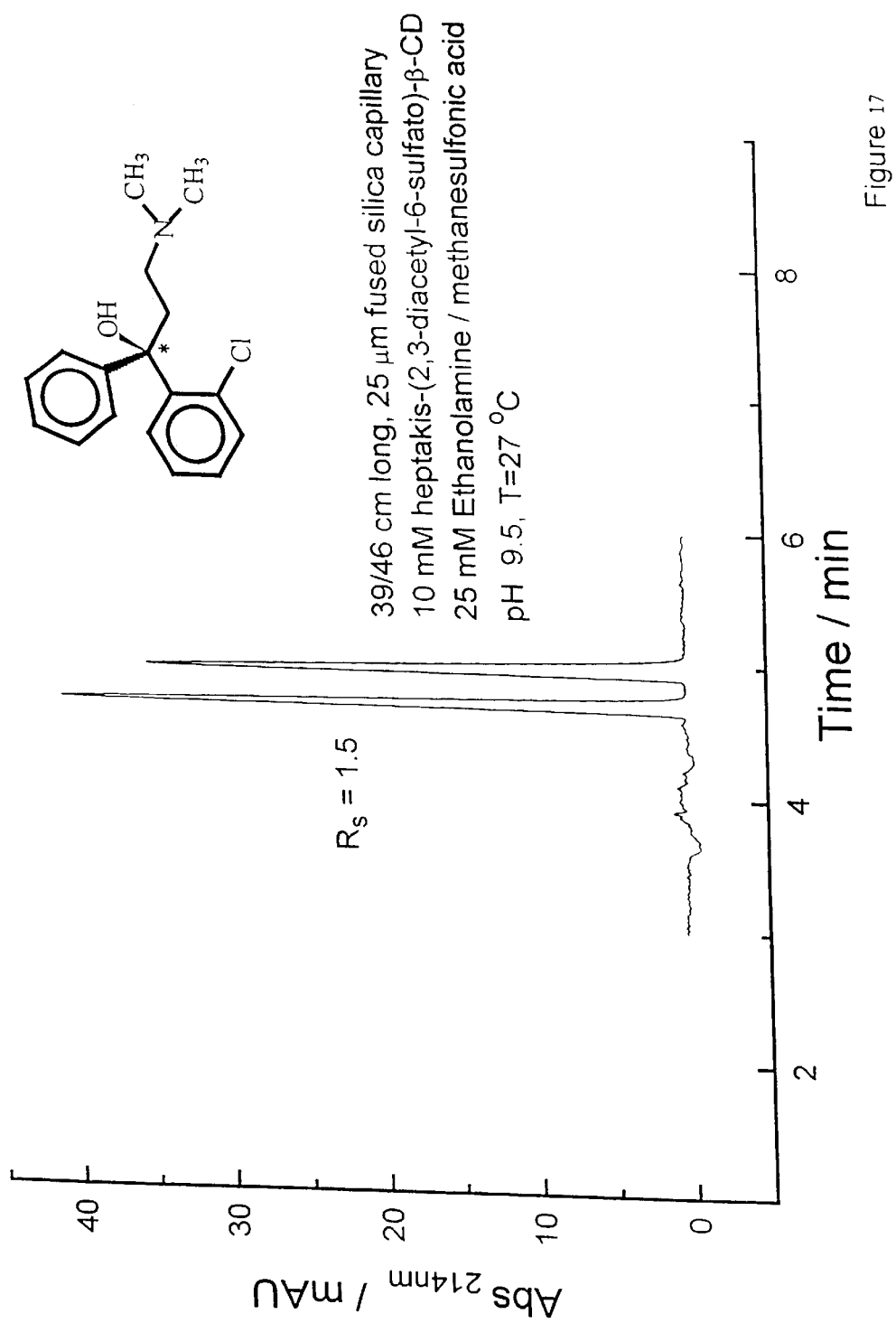
FIG. 17 is an electropherogram of racemic chlophedianol separated with the single-isomer heptakis-(2,3-diacetyl-6-sulfato)-β-cyclodextrin.
Figure 18:
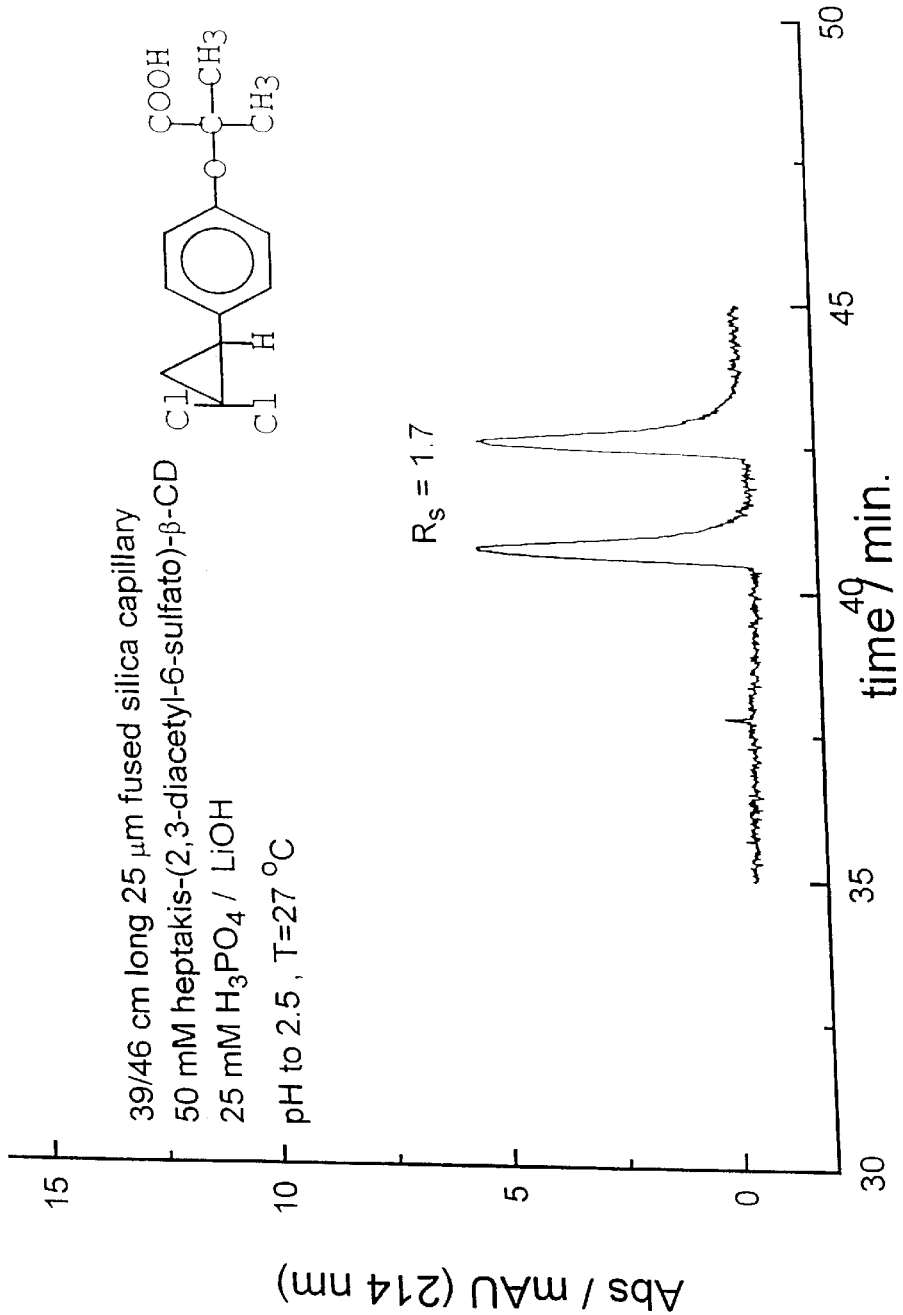
FIG. 18 is an electropherogram of racemic ciprofibrate separated with the single-isomer heptakis-(2,3-diacetyl-6-sulfato)-β-cyclodextrin.

Electropherograms illustrating the chiral separation of the above enantiomeric analytes are shown in FIGS. 16, 17 and 18. FIG. 16 shows the separation of the enantiomers of α-methyl-α-phenyl-succinimide in the high pH BE containing 5mM heptakis-(2,3-diacetyl-6-sulfato)-β-cyclodextrin. FIG. 17 shows the separation of the enantiomers of chlophedianol in the high pH BE containing 10 mM heptakis-(2,3-diacetyl-6-sulfato)-β-cyclodextrin. FIG. 18 shows the separation of the enantiomers of ciprofibrate in the high pH BE containing 10 mM heptakis-(2,3-diacetyl-6-sulfato)-β-cyclodextrin. Apparent from all three electropherograms are the separate and well-defined peaks of the eluted analyte enantiomers, which demonstrate the ability of the functionalized cyclodextrins to alter the mobility of the analyte enantiomers.

Example 5
Electrophoretic Separations using Heptakis-(6-sulfato)-β-cyclodextrin

Following the procedure of Example 4, low pH and high pH BEs were prepared using the heptakis-(6-sulfato)-β-cyclodextrin of Example 2. 250 μL samples of three racemic analytes (benzoin (a neutral analyte), labetalol (a basic analyte), fenoprofen (an acidic analyte)) were prepared at 0.5 mM concentrations in the P/ACE microvials with the respective HS-βCD BEs.

Figure 19:
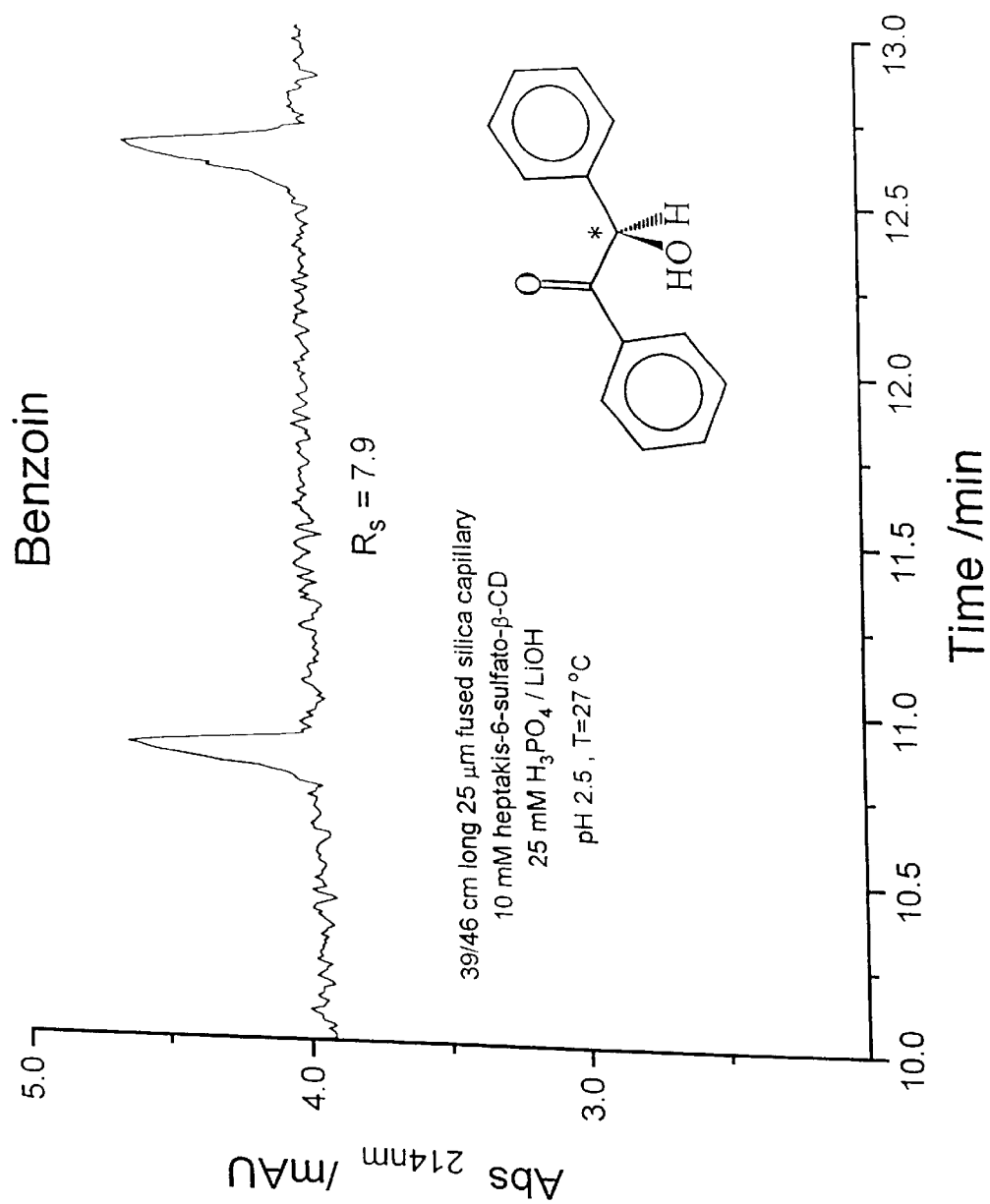
FIG. 19 is an electropherogram of racemic benzoin separated with the single-isomer hepta-6-sulfato-β-cyclodextrin.
Figure 20:
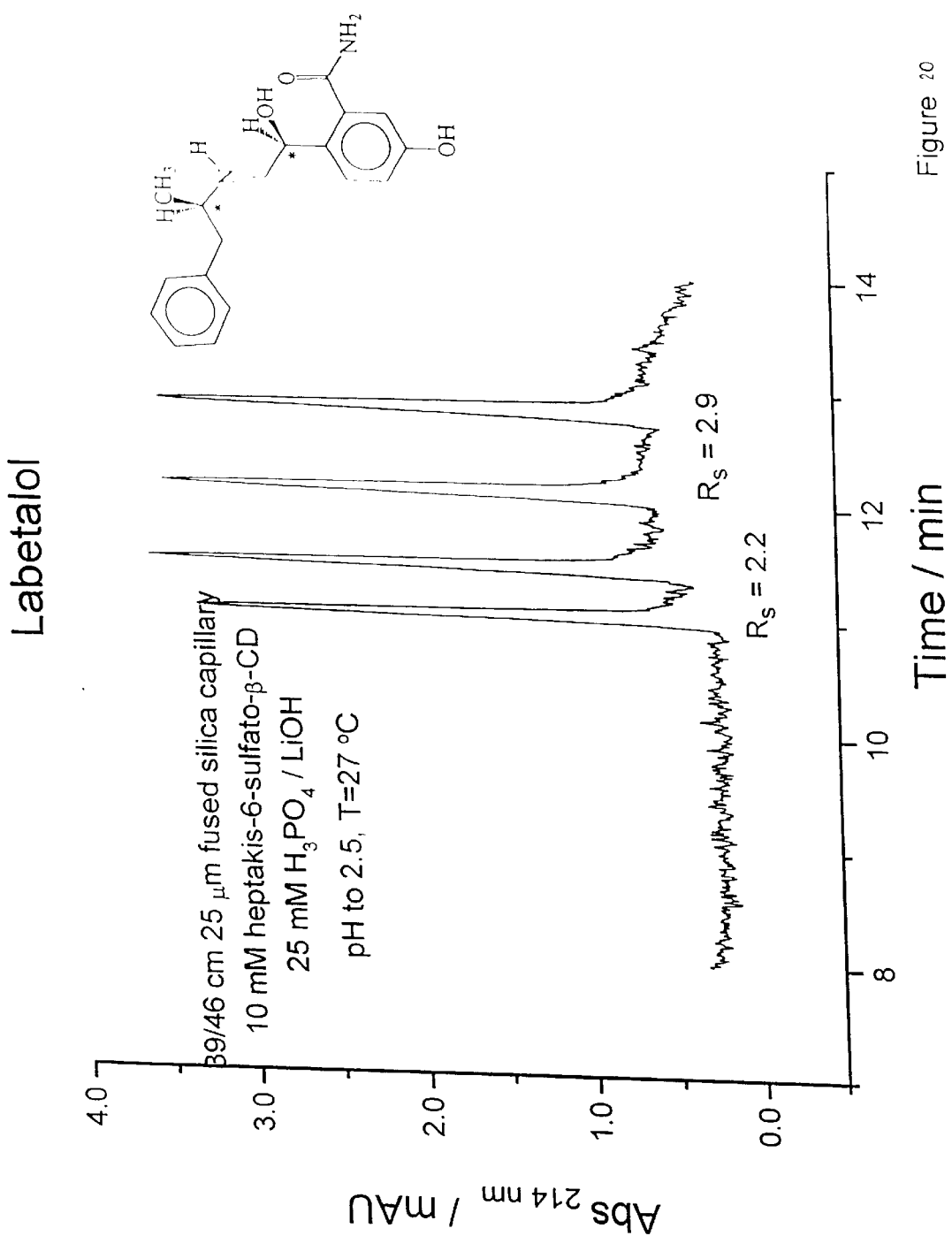
FIG. 20 is an electropherogram of racemic labetalol separated with the single-isomer hepta-6-sulfato-β-cyclodextrin.
Figure 21:
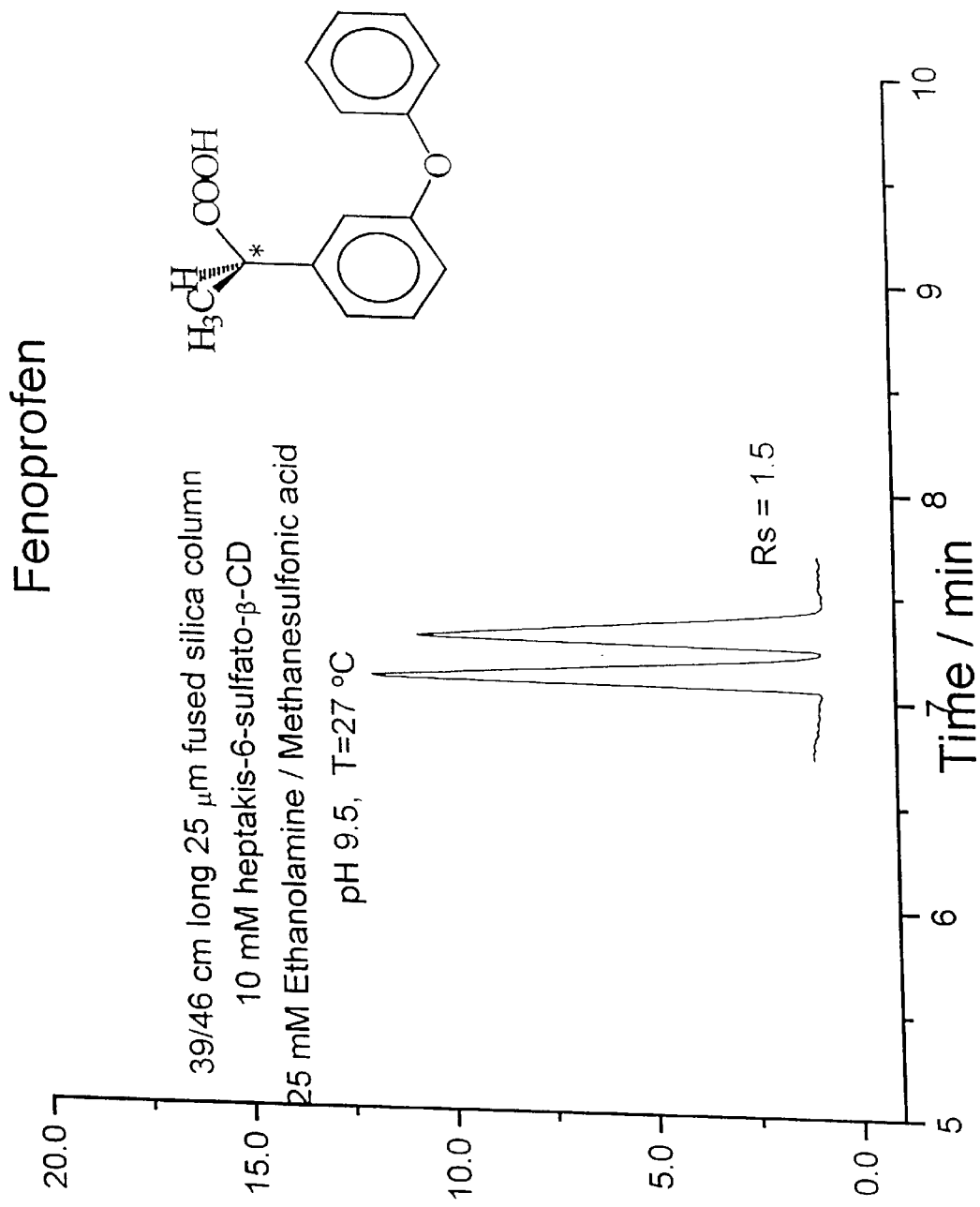
FIG. 21 is an electropherogram of racemic fenoprofen separated with the single-isomer hepta-6-sulfato-β-cyclodextrin.

Electropherograms illustrating the separation of the above enantiomers are shown in FIGS. 19, 20 and 21. FIG. 19 shows the separation of the enantiomers of benzoin in the low pH BE containing 10 mM hepta-6-sulfato-β-cyclodextrin. FIG. 20 shows the separation of the enantiomers of labetalol in the low pH BE containing 10 mM hepta-6-sulfato-β-cyclodextrin. FIG. 21 shows the separation of the enantiomers of fenoprofen in the high pH BE containing 10 mM hepta-6-sulfato-β-cyclodextrin. As in Example 4, the eluted analyte enantiomers can be seen as separate and well-defined peaks.

Figure 22:
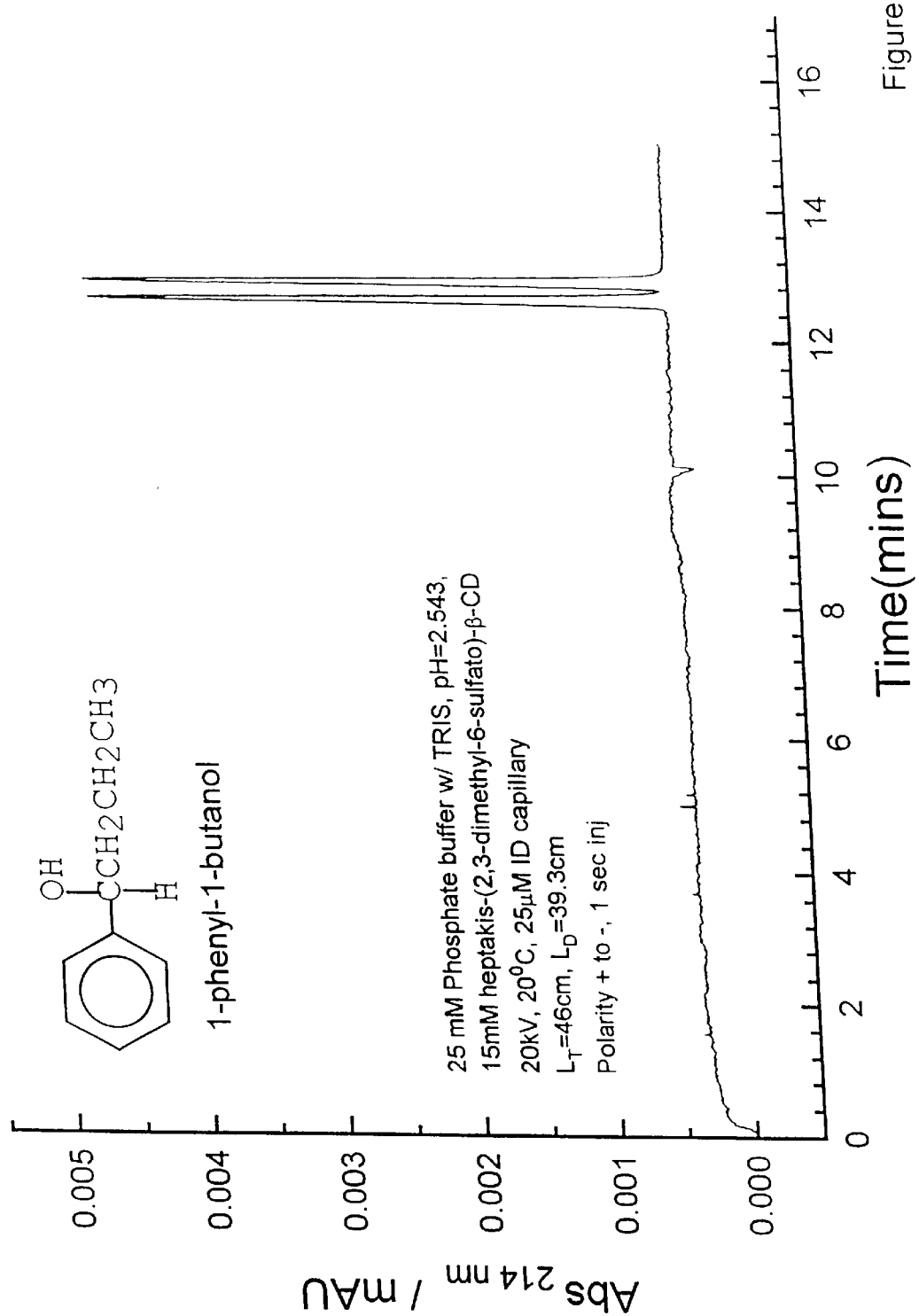
FIG. 22 is an electropherogram of racemic 1-phenyl-1-butanol separated with the single-isomer heptakis-(2,3-dimethyl-6-sulfato)-β-cyclodextrin.
Figure 23:
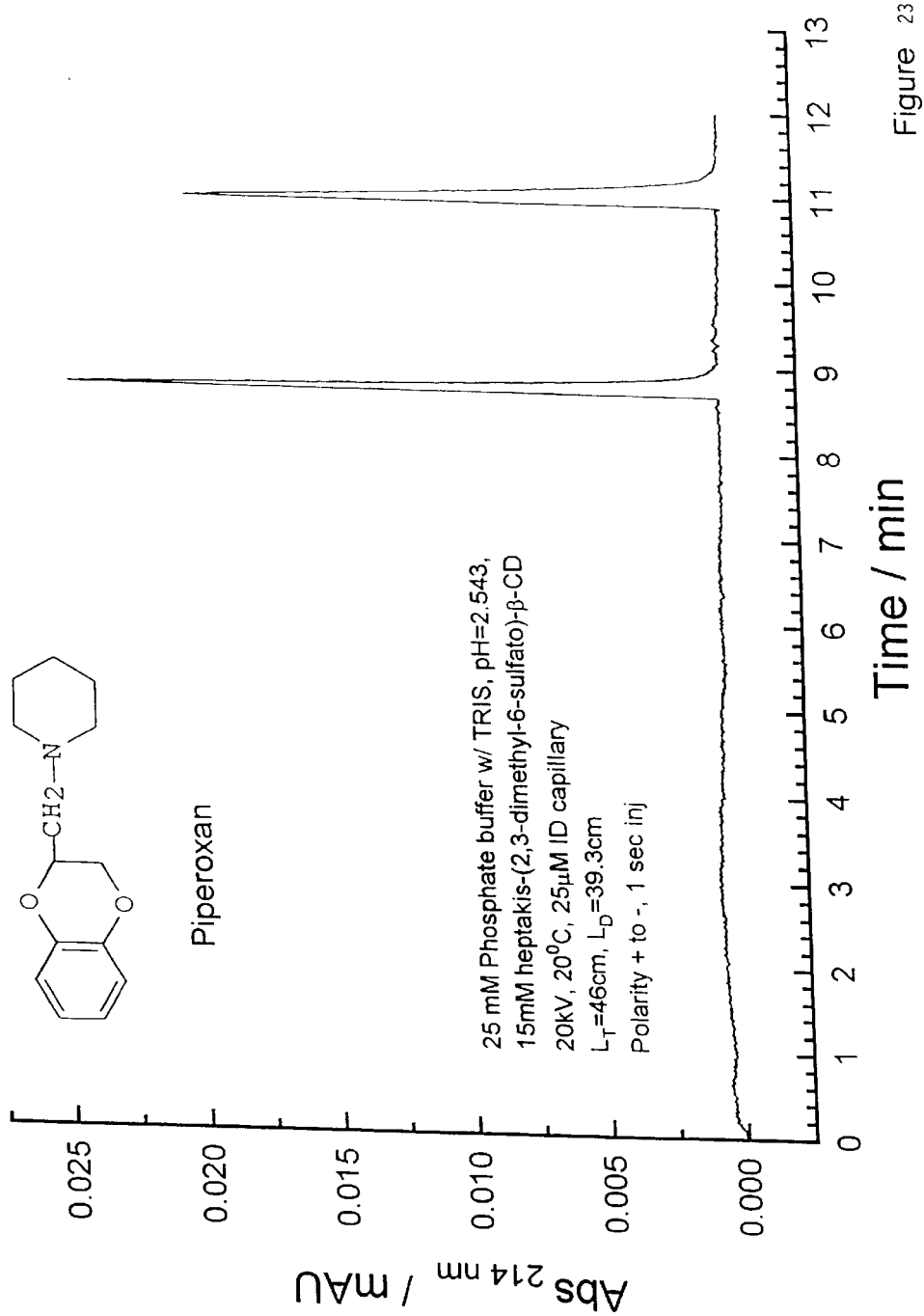
FIG. 23 is an electropherogram of racemic piperoxan separated with the single-isomer heptakis-(2,3-dimethyl-6-sulfato)-β-cyclodextrin.
Figure 24:
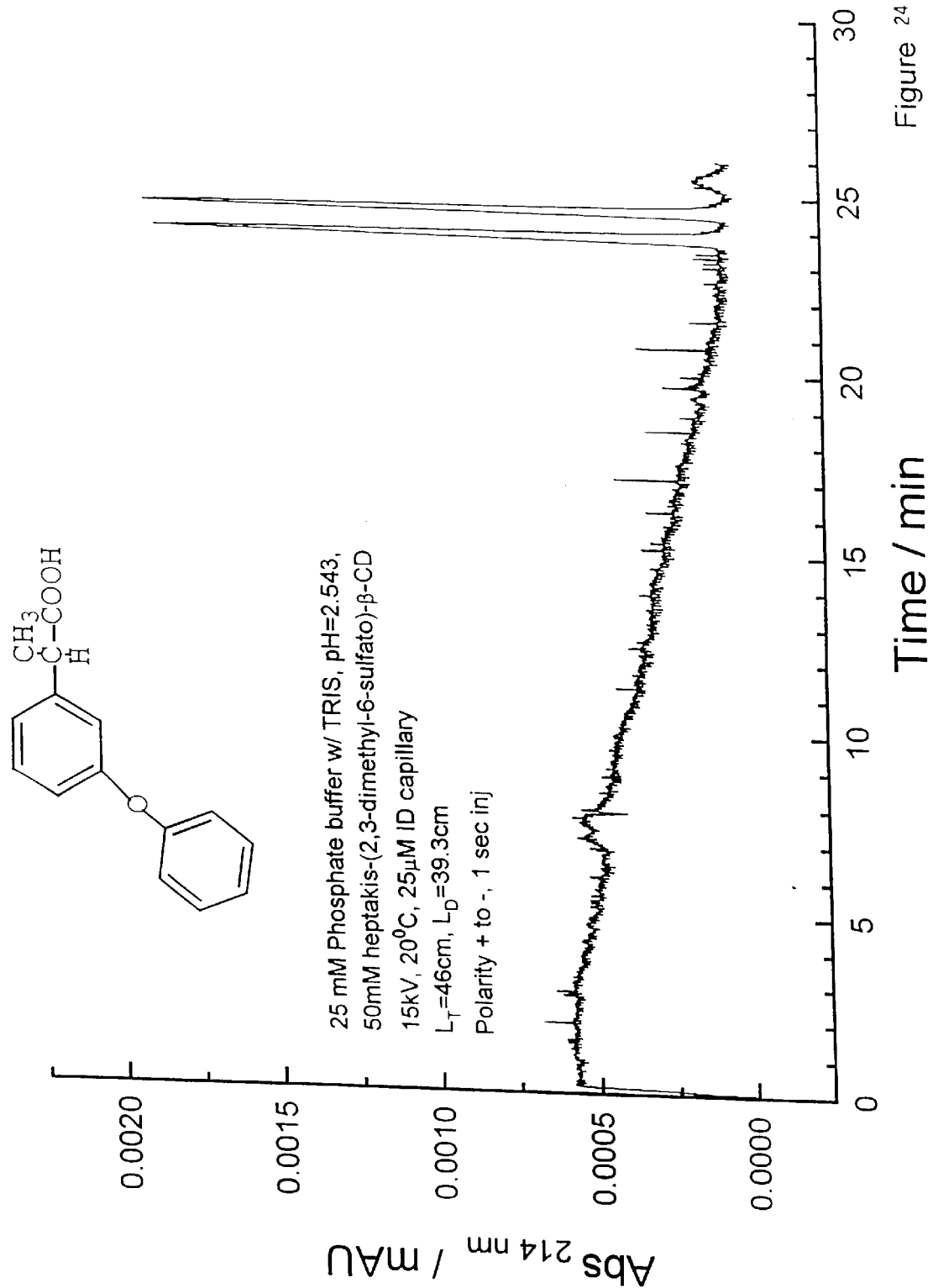
FIG. 24 is an electropherogram of racemic fenoprofen separated with the single-isomer heptakis-(2,3-dimethyl-6-sulfato)-β-cyclodextrin.

Example 6
Electrophoretic Separations using Heptakis-(2,3-dimethyl-6-sulfato)-β-cyclodextrin Following the procedure of Example 4, low pH and high pH BEs were prepared using heptakis-(2,3-dimethyl-6- sulfato)-β-cyclodextrin of Example 3. 250 μL samples of three racemic analytes (1-phenyl-1-butanol (a neutral analyte), piperoxan (a basic analyte), fenoprofen (an acidic analyte)) were prepared at 0.5 mM concentrations in the P/ACE microvials with the respective HS-βCD BEs. The electropherograms illustrating the separation of the above enantiomers are shown in FIGS. 22, 23 and 24. FIG. 22 shows the separation of the enantiomers of 1-phenyl-1-butanol in the low pH BE containing 15 mM heptakis-(2,3-dimethyl-6-sulfato)-β-cyclodextrin. FIG. 23 shows the separation of the enantiomers of piperoxan in the low pH BE containing 15 mM heptakis-(2,3-dimethyl-6-sulfato)-β-cyclodextrin. FIG. 24 shows the separation of the enantiomers of fenoprofen in the low pH BE containing 50 mM heptakis-(2,3-dimethyl-6-sulfato)-β-cyclodextrin.

Prophetic Example 7
Synthesis of Heptakis-(3,6-diacetyl-2-sulfato)-β-cyclodextrin Heptakis-(3,6-diacetyl-2-sulfato)-β-cyclodextrin is prepared following the reaction scheme shown in FIG. 4. Briefly, 79 mmol imidazole and 7.9 mmol 4-N,N-dimethylamino pyridine are added to warm N,N-dimethylformamide, followed by 8.8 mmol dried β-cyclodextrin. 66 mmol triethylsilyl chloride is diluted threefold in ethyl acetate and dropped into the β-cyclodextrin solution. Once the reaction is complete, excess triethylsilyl chloride is destroyed by methanol, the reaction mixture is poured into a fourfold volume of dichloromethane and the resulting solution is poured into a tenfold volume of water. The phases are separated, the aqueous wash is repeated and the crude product is purified by preparative gradient elution column chromatography as in Example 1. 8.8 mmol of the dried, purified intermediate is then dissolved in warm N,N-dimethylformamide which contains up to 50% tetrahydrofuran, 160 mmol imidazole and 16 mmol 4-N,N-dimethylamino pyridine and 140 mmol t-butyldimethylsilyl chloride. Once the silylation reaction is complete, excess t-butyldimethylsilyl chloride is destroyed by methanol, the reaction mixture is poured into a sixfold volume of hexane. The phases are separated and the hexane layer is poured into a tenfold volume of water. The phases are separated, the aqueous wash is repeated and the crude product is purified by preparative gradient elution column chromatography as in Example 1.

The purified heptakis-(2-t-butyldimethylsilyl-6-triethylsilyl)-β-cyclodextrin is then dissolved in dilute acetic acid-containing tetrahydrofuran to remove the triethylsilyl protecting groups. After work-up, the crude product is purified by preparative gradient elution column chromatography as in Example 1. The purified intermediate is then peracetylated with acetic anhydride as described in Example 1. The purified heptakis-(2-t-butyldimethylsilyl-3,6-diacetyl)-β-cyclodextrin is then reacted with boron trifluoride etherate as described in Example 1 to remove the t-butyldimethylsilyl protecting groups. The crude product is repurified by gradient elution preparative column chromatography on silica gel as in Example 1. Finally, the purified heptakis-(3,6-diacetyl)-β-cyclodextrin is reacted with $SO_3$·pyridine in DMF as in Example 1 to completely sulfate the exposed hydroxyl groups of the cyclodextrin as described in Example 1. Progress of the reaction is monitored and work-up is completed as in Example 1 to obtain pure heptakis-(3,6-diacetyl-2-sulfato)-β-cyclodextrin.

Prophetic Example 8
Synthesis of Hepta-3-sulfato-β-cyclodextrin

Hepta-3-sulfato-β-cyclodextrin is prepared following the reaction scheme shown in FIG. 2. First, hepta-6-t-butyldimethylsilyl-β-cyclodextrin is prepared and purified as in Example 1. Next, 8.8 mmol of the dried, purified intermediate is then dissolved in warm N,N-dimethylformamide which contains up to 50% tetrahydrofuran, 160 mmol imidazole, 16 mmol 4-N,N-dimethylamino pyridine and 140 mmol t-butyldimethylsilyl chloride. Once the reaction is complete, excess t-butyldimethylsilyl chloride is destroyed by methanol, the reaction mixture is poured into a sixfold volume of hexane. The phases are separated and the hexane layer is poured into a tenfold volume of water. The phases are separated, the aqueous wash is repeated and the crude product is purified by preparative gradient elution column chromatography as in Example 1. The purified heptakis-(2,6-di(t-butyldimethylsilyl))-β-cyclodextrin is then sulfated with $SO_3$·pyridine as in Example 1. Finally, the t-butyldimethylsilyl protecting groups are removed with aqueous ethanolic HF as in Example 3 to yield pure hepta-3-sulfato-β-cyclodextrin.

Example 9
Synthesis of Heptakis-(3-methyl-2,6-disulfato)-β-cyclodextrin

Figure 25:
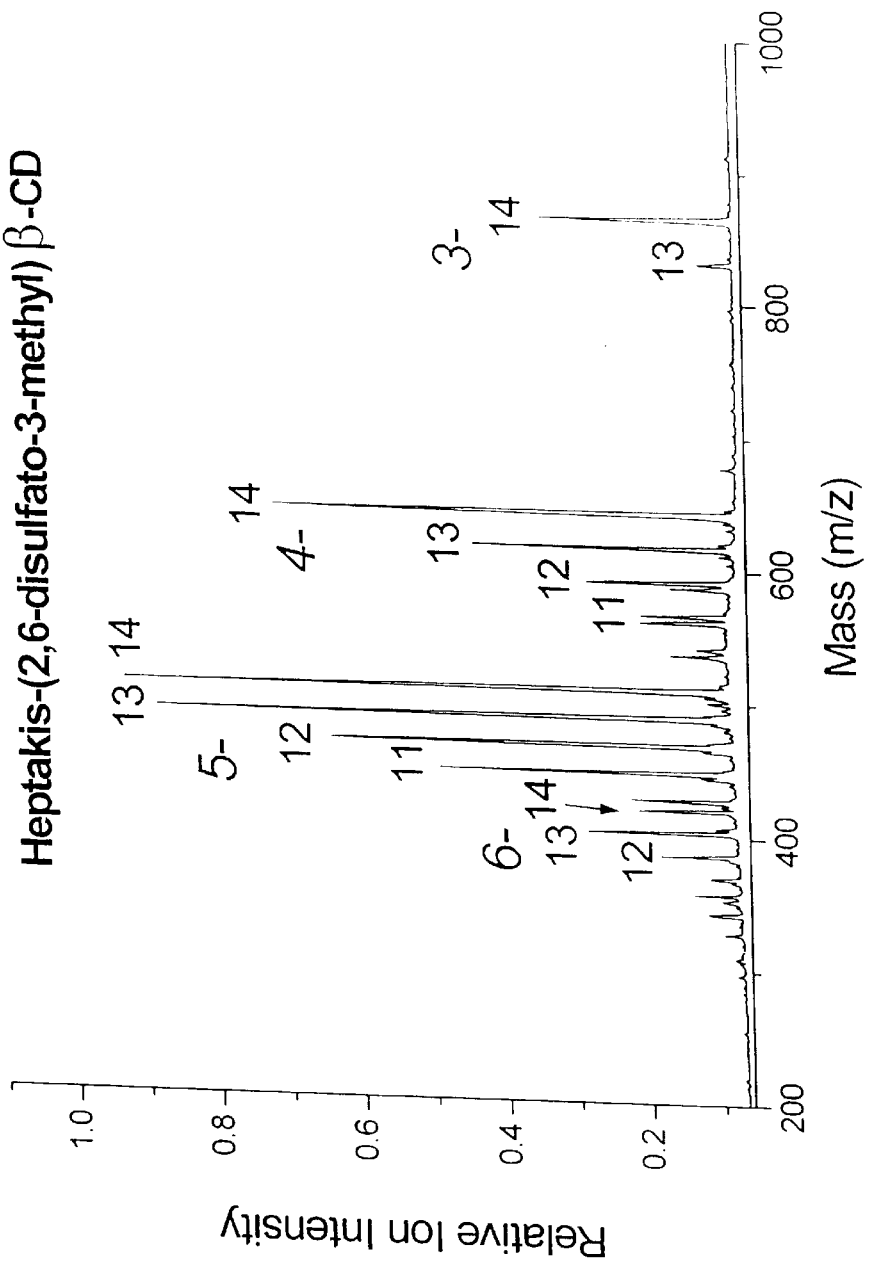
FIG. 25 is an electrospray-ionization mass spectrum of the single-isomer heptakis-(3-methyl-2,6-disulfato)-β-cyclodextrin.
Figure 26:
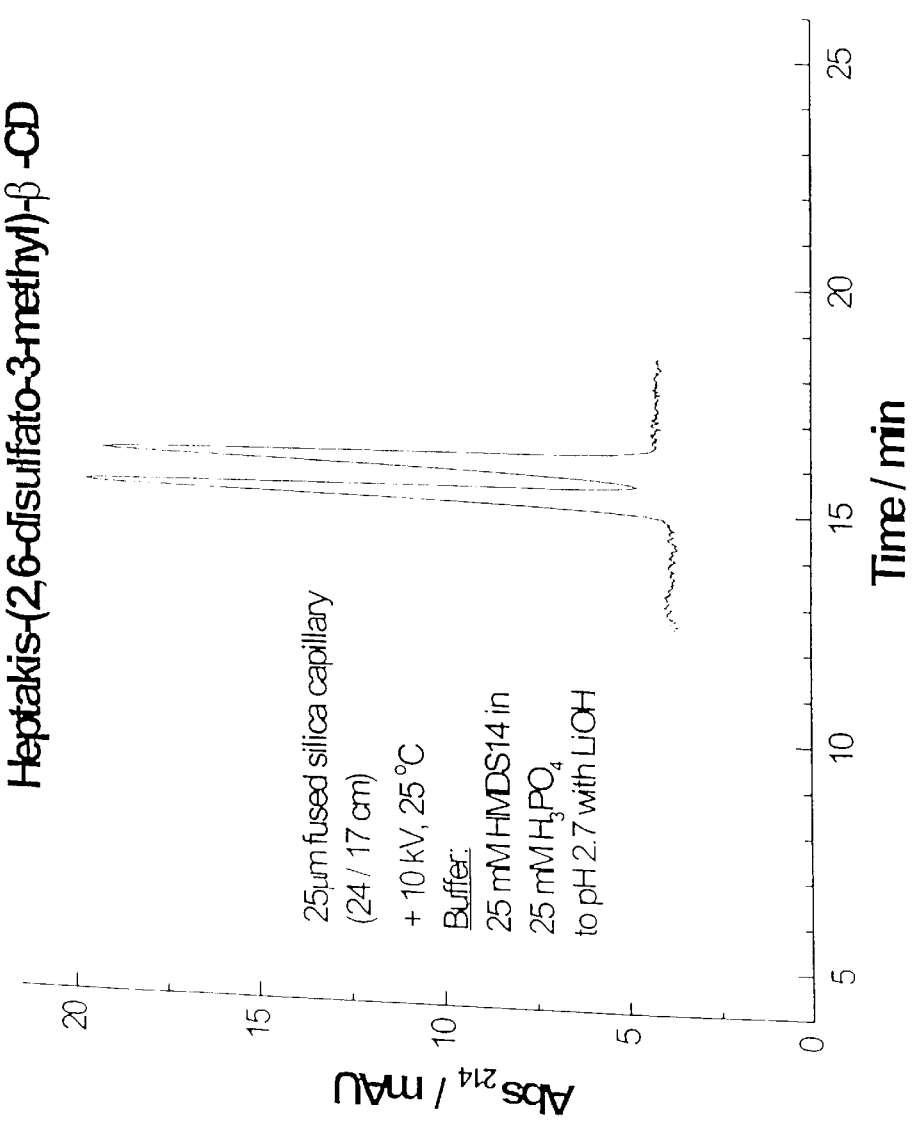
FIG. 26 is an electropherogram of racemic isoproterenol separated with the single-isomer heptakis-(3-methyl-2,6-disulfato)-β-cyclodextrin.

Heptakis-(3-methyl-2,6-disulfato)-β-cyclodextrin was prepared following the reaction scheme shown in FIG. 5. First, heptakis-(2,6-di(t-butyldimethylsilyl))-β-cyclodextrin was prepared and purified as in Example 8. Next, 7 mmol of heptakis-(2,6-di(t-butyldimethylsilyl))-β-cyclodextrin was methylated with NaH and methyliodide as in Example 3. 4 mmol of the purified intermediate was dissolved in tetrahydrofuran, to which 60 mmol tetrabutylammonium fluoride was added, and the solution refluxed for two hours to remove the t-butyldimethylsilyl protecting groups. After work-up, the crude reaction mixture containing hepta-3-methyl-β-cyclodextrin was once again repurified by preparative gradient elution column chromatography using the n-hexane:ethyl acetate:ethanol eluent system as in Example 1 and the pure final cyclodextrin intermediate was sulfated with $SO_3$·pyridine as described in Example 1. An electrospray ionization mass spectrum of the heptakis-(3-methyl-2,6-disulfato)-β-cyclodextrin sample is shown in FIG. 25. An electropherogram demonstrating the separation of the enantiomers of isoproterenol using heptakis-(3-methyl-2,6-disulfato)-β-cyclodextrin, following the procedure described above, is shown in FIG. 26.

Prophetic Example 10
Synthesis of Heptakis-(3,6-disulfato)-β-cyclodextrin

Heptakis-(3,6-disulfato)-β-cyclodextrin is prepared following the reaction scheme shown in FIG. 6. First, hepta-6-triethylsilyl-β-cyclodextrin is prepared and purified as in Example 7. Heptakis-(2-t-butyldimethylsilyl-6-triethylsilyl)-β-cyclodextrin is prepared and purified as in Example 7. Next, the triethylsilyl protecting groups are removed from the purified intermediate as in Example 7 to yield hepta-2-t-butyldimethylsilyl-β-cyclodextrin, which is purified as in Example 7. The intermediate is then sulfated with $SO_3$·pyridine as described in Example 1 and, finally, the t-butyldimethylsilyl protecting groups are removed with aqueous ethanolic HF as in Example 3 yielding the desired product, heptakis-(3,6-disulfato)-β-cyclodextrin.

Prophetic Example 11
Synthesis of Heptakis-2,3-disulfato-β-cyclodextrin

Heptakis-(2,3-disulfato)-β-cyclodextrin is prepared by first synthesizing and purifying, as in Example 1, hepta-6-t-butyldimethylsilyl-β-cyclodextrin. This intermediate is then persulfated with $SO_3$·pyridine as in Examples 9 and 10, followed by the removal of the t-butyldimethylsilyl protecting groups with aqueous ethanolic HF as in Example 3 yielding the desired product, heptakis-(2,3-disulfato)-β-cyclodextrin.

Example 12

Synthesis of Octakis-6-sulfato-γ-cyclodextrin

Figure 27:
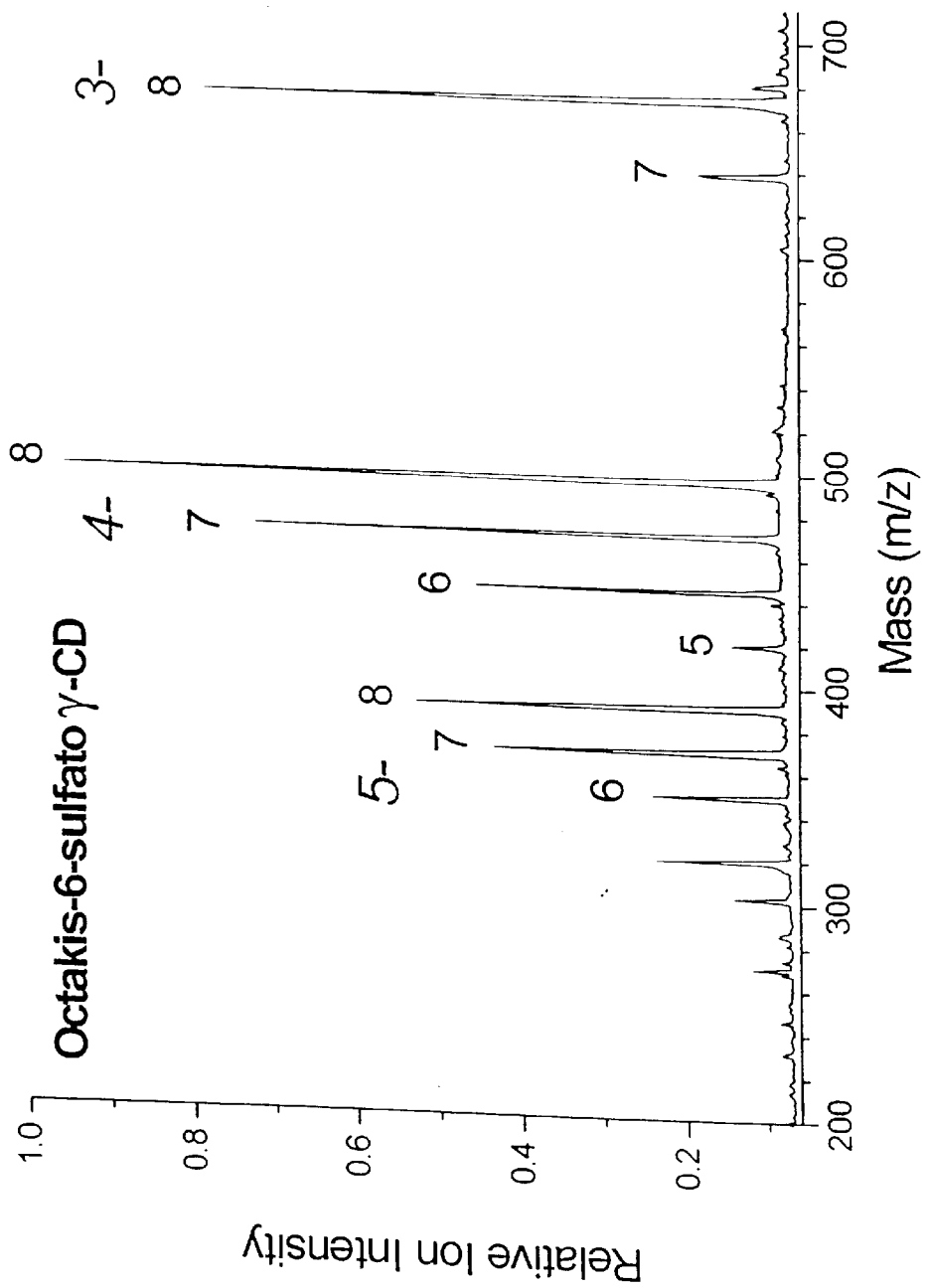
FIG. 27 is an electrospray-ionization mass spectrum of the single-isomer octakis-6-sulfato-γ-cyclodextrin.
Figure 28:
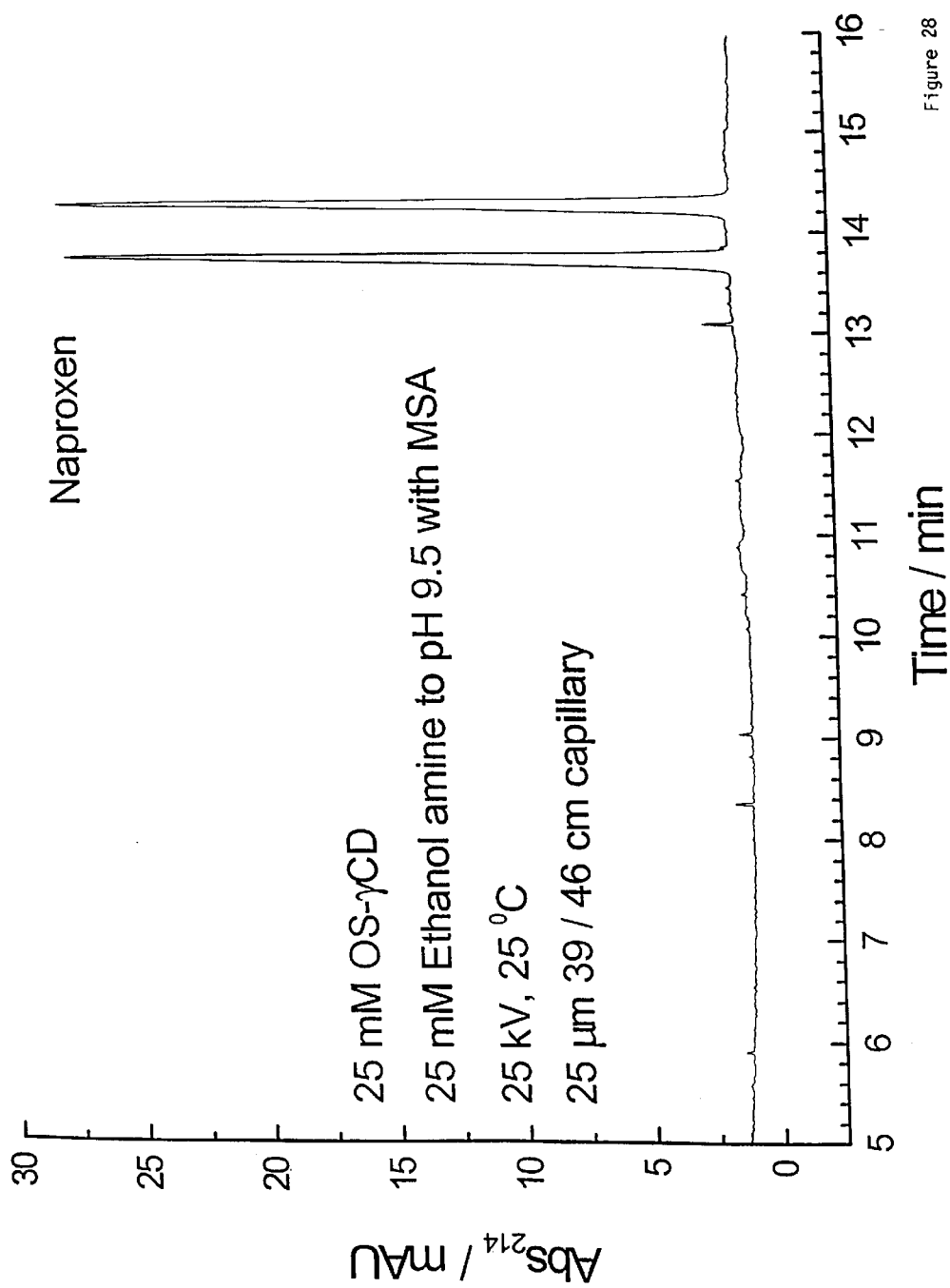
FIG. 28 is an electropherogram of racemic naproxen separated with the single-isomer octakis-6-sulfato-γ-cyclodextrin.

Octakis-6-sulfato-γ-cyclodextrin was prepared by first synthesizing and purifying octakis-(2,3-diacetyl-6-sulfato)-γ-cyclodextrin from γ-cyclodextrin following the procedure described in Example 1. This intermediate was then deacetylated using the procedure described in Example 2 yielding the desired product, octakis-6-sulfato-γ-cyclodextrin. An electrospray-ionization mass spectrum of the octakis-(2,3-diacetyl-6-sulfato)-γ-cyclodextrin sample is shown in FIG. 27. An electropherogram demonstrating the separation of the enantiomers of naproxen using octakis-6-sulfato-γ-cyclodextrin, following the procedure described above, is shown in FIG. 28.

I claim:

1. A single-isomer cyclodextrin composition, which comprises substantially pure cyclodextrin derivatives having the formula:

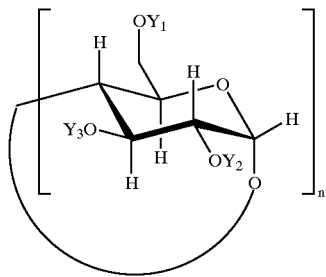

wherein:

n is a single integer ranging from 6 to 12;
$Y_1$ is $SO_3^-$;
$Y_2$ is H, $CH_3$, $CH_2CH_3$, $CH_2CHOHCH_3$, $CH_2CN$, or $OCCH_3$;
$Y_3$ is H, $CH_3$, $CH_2CH_3$, $CH_2CHOHCH_3$, $CH_2CN$, or $OCCH_3$; and
the cyclodextrin composition has an isomeric purity of at least 80 mole %.

2. A single-isomer cyclodextrin composition, which comprises substantially pure cyclodextrin derivatives having the formula:

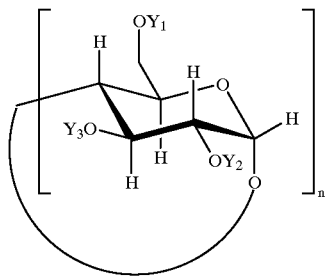

wherein:

n is a single integer ranging from 6 to 12;
$Y_2$ is $SO_3^-$;
$Y_1$ is H, $CH_3$, $CH_2CH_3$, $CH_2CHOHCH_3$, $CH_2CN$, or $OCCH_3$;
$Y_3$ is H, $CH_3$, $CH_2CH_3$, $CH_2CHOHCH_3$, $CH_2CN$, or $OCCH_3$; and
the cyclodextrin composition has an isomeric purity of at least 80 mole %.

3. A single-isomer cyclodextrin composition, which comprises substantially pure cyclodextrin derivatives having the formula:

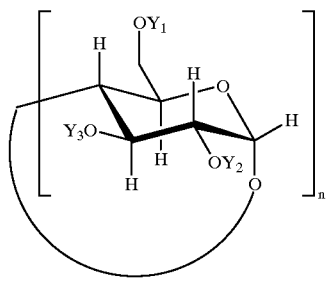

wherein:

n is a single integer ranging from 6 to 12;
$Y_3$ is $SO_3^-$;
$Y_1$ is H, $CH_3$, $CH_2CH_3$, $CH_2CHOHCH_3$, $CH_2CN$, or $OCCH_3$;
$Y_2$ is H, $CH_3$, $CH_2CH_3$, $CH_2CHOHCH_3$, $CH_2CN$, or $OCCH_3$ and
the cyclodextrin composition has an isomeric purity of at least 80 mole %.

4. A single-isomer cyclodextrin composition, which comprises substantially pure cyclodextrin derivatives having the formula:

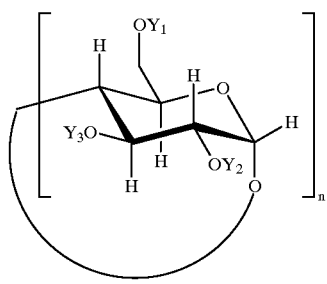

wherein n is a single integer ranging from 6 to 12;
$Y_1$ and $Y_2$ is $SO_3^-$;
$Y_3$ is H, $CH_3$, $CH_2CH_3$, $CH_2CHOHCH_3$, $CH_2CN$, or $OCCH_3$; and
the cyclodextrin composition has an isomeric purity of at least 80 mole %.

5. A single-isomer cyclodextrin composition, which comprises substantially pure cyclodextrin derivatives having the formula:

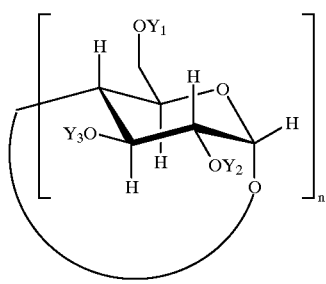

wherein:

n is a single integer ranging from 6 to 12;

$Y_1$ and $Y_3$ is $SO_3^-$;

$Y_2$ is H, $CH_3$, $CH_2CH_3$, $CH_2CHOHCH_3$, $CH_2CN$, or $OCCH_3$; and the cyclodextrin composition has an isomeric purity of at least 80 mole %.

6. The composition of claim 1, wherein $Y_2$ and $Y_3$ are the same.

7. The composition of claim 1, wherein $Y_2$ and $Y_3$ are the different.

8. The composition of claim 2, wherein $Y_1$ and $Y_3$ are the same.

9. The composition of claim 2, wherein $Y_1$ and $Y_3$ are the different.

10. The composition of claim 3, wherein $Y_1$ and $Y_2$ are the same.

11. The composition of claim 3, wherein $Y_1$ and $Y_2$ are the different.

12. A single-isomer cyclodextrin composition, which comprises substantially pure hepta-6-sulfato-β-cyclodextrin, wherein the cyclodextrin composition has an isomeric purity of at least 80 mole %.

13. A single-isomer cyclodextrin composition, which comprises substantially pure heptakis-(2,3-diacetyl-6-sulfato)-β-cyclodextrin, wherein the cyclodextrin composition has an isomeric purity of at least 80 mole %.

14. A single-isomer cyclodextrin composition, which comprises substantially pure heptakis-(2,3-dimethyl-6-sulfato)-β-cyclodextrin, wherein the cyclodextrin composition has an isomeric purity of at least 80 mole %.

15. A single-isomer cyclodextrin composition, which comprises substantially pure octa-6-sulfato-γ-cyclodextrin, wherein the cyclodextrin composition has an isomeric purity of at least 80 mole %.

16. A single-isomer cyclodextrin composition, which comprises substantially pure octakis-(2,3-diacetyl-6-sulfato)-γ-cyclodextrin, wherein the cyclodextrin composition has an isomeric purity of at least 80 mole %.

17. A single-isomer cyclodextrin composition, which comprises substantially pure octakis-(2,3-dimethyl-6-sulfato)-γ-cyclodextrin, wherein the cyclodextrin composition has an isomeric purity of at least 80 mole %.

* * * * *